United States Patent
Botár et al.

(10) Patent No.: US 10,894,096 B2
(45) Date of Patent: Jan. 19, 2021

(54) 3,6,9, 15-TETRAAZA-BICYCLO [9.3.1]PENTADECA-1(14), 11(15), 12-TRIENE BASED COMPOUNDS AND THEIR APPLICATION AS LIGANDS OF ESSENTIAL METAL ION BASED MRI AND 52MN BASED PET CONTRAST AGENTS

(71) Applicant: DEBRECENI EGYETEM, Debrecen (HU)

(72) Inventors: Richárd Botár, Emöd (HU); Zoltán Garda, Túrricse (HU); Tamás Fodor, Miskolc (HU); Ferenc Krisztián Kálmán, Debrecen (HU); Viktória Nagy, Debrecen (HU); Gyula Tircsó, Debrecen (HU); Imre Tóth, Debrecen (HU)

(73) Assignee: DEBRECENI EGYETEM, Debrecen (HU)

( * ) Notice: Subject to any disclaimer, the term of this patent is extended or adjusted under 35 U.S.C. 154(b) by 0 days.

(21) Appl. No.: 16/736,130

(22) Filed: Jan. 7, 2020

(65) Prior Publication Data
US 2020/0157099 A1    May 21, 2020

Related U.S. Application Data

(63) Continuation of application No. 15/778,457, filed as application No. PCT/HU2016/000073 on Nov. 25, 2016, now Pat. No. 10,568,976.

(30) Foreign Application Priority Data

Nov. 26, 2015   (HU) .................... 1500564
Oct. 18, 2016   (HU) .................... 1600581

(51) Int. Cl.
| | |
|---|---|
| C07D 257/02 | (2006.01) |
| C07F 15/00 | (2006.01) |
| A61K 51/04 | (2006.01) |
| C07D 471/08 | (2006.01) |
| A61B 5/055 | (2006.01) |
| A61K 49/10 | (2006.01) |
| C07D 471/06 | (2006.01) |

(52) U.S. Cl.
CPC .......... *A61K 51/0485* (2013.01); *A61B 5/055* (2013.01); *A61K 49/106* (2013.01); *C07D 471/06* (2013.01); *C07D 471/08* (2013.01); *A61K 2123/00* (2013.01)

(58) Field of Classification Search
CPC ........ C07D 257/02; C07F 15/02; A61K 49/06
USPC .............. 540/465, 474; 424/9.363
See application file for complete search history.

(56) References Cited

U.S. PATENT DOCUMENTS

| | | | |
|---|---|---|---|
| 5,316,756 A | 5/1994 | Gries et al. | |
| 5,334,371 A | 8/1994 | Gries et al. | |
| 5,385,893 A | 1/1995 | Kiefer et al. | |
| 5,480,990 A | 1/1996 | Kiefer et al. | |
| 5,693,310 A | 12/1997 | Gries et al. | |
| 8,268,810 B2 | 9/2012 | Port | |
| 10,568,976 B2* | 2/2020 | Botar | C07D 471/08 |
| 2010/0092396 A1 | 4/2010 | Kovacs et al. | |
| 2011/0092806 A1 | 4/2011 | Port et al. | |
| 2014/0206862 A1 | 7/2014 | Green et al. | |
| 2015/0209452 A1 | 7/2015 | Mirica et al. | |
| 2018/0282333 A1 | 10/2018 | Botár et al. | |
| 2018/0354969 A1 | 12/2018 | Botár et al. | |

FOREIGN PATENT DOCUMENTS

| | | |
|---|---|---|
| EP | 0 130 934 A1 | 1/1985 |
| EP | 0 263 059 A2 | 4/1988 |
| WO | 90/11282 A1 | 10/1990 |
| WO | 94/26276 A1 | 11/1994 |
| WO | 99/65905 A1 | 12/1999 |
| WO | 2011/073371 A1 | 6/2011 |

OTHER PUBLICATIONS

Weber, E., et al. Ligandstruktur und Komplexierung, V[1)] Neue Kronenäther und ihre Alkalimetallion-Komplexe. [Ligand Structure and Complexation, V[1)] New Crown Ethers and Their Alkali Metal Ion Complexes]. Chemische Berichte, 1976. vol. 109, No. 5, pp. 1803-1831 (with partial English translation).

Oschepkov, M.S., et al. Synthesis of Azacrown Ethers and Benzocryptands by Macrocyclization of Podands at High Concentrations of Reactants. Russian Chemical Bulletin, International Edition. 2011. vol. 60, No. 3, pp. 478-485.

Aime, S. et al. Designing Novel Contrast Agents for Magnetic Resonance Imaging. Synthesis and Relaxometric Characterization of three Gadolinium(III) Complexes Based on Functionalized Pyridine-Containing Macrocyclic Ligands. Helvetica Chimica Acta. 2003. vol. 86, pp. 615-632.

(Continued)

*Primary Examiner* — Charanjit Aulakh
(74) *Attorney, Agent, or Firm* — Smith, Gambrell & Russell, LLP

(57) ABSTRACT

A compound of the following general formula (I), and isomers, physiologically acceptable salts, and complexes thereof, for use as a contrast agent in diagnostic imaging:

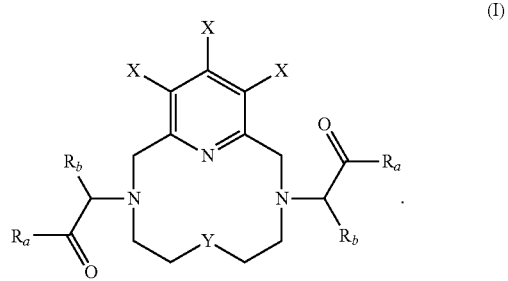

(I)

16 Claims, No Drawings

(56) References Cited

OTHER PUBLICATIONS

Kim, W.D. et al.: Synthesis, crystal structure, and potentiometry of pyridine- containing tetraza macrocyclic ligands with acetate pendant arms. Inorganic Chemistry. 1995. vol. 34, pp. 2225-2232.
Rojas-Quijano, F.A. et al.: Lanthanide (III) complexes of tris(amide) PCTA derivatives as potential bimodal magnetic resonance and optical imaging agents. Chemistry, a European Journal. 2009. vol. 15, pp. 13188-13200.
International Search Report mailed relative to PCT/HU2016/000073, dated Apr. 5, 2017 (5 pages).
Written Opinion of the International Searching Authority, mailed relative to PCT/HU2016/000073, dated Apr. 5, 2017 (8 pages).
International Search Report mailed relative to PCT/HU2016/000074, dated Feb. 10, 2017 (4 pages).
Written Opinion of the International Searching Authority, mailed relative to PCT/HU2016/000074, dated Feb. 10, 2017 (6 pages).
International Search Report mailed relative to PCT/HU2016/000075, dated Feb. 6, 2017 (5 pages).
Written Opinion of the International Searching Authority, mailed relative to PCT/HU2016/000075, dated Feb. 6, 2017 (6 pages).
Ema's final opinion confirms restrictions on use of linear gadolinium agents in body scans, *European Medicines Agency Science Medicines Health*, EMA/625317/2017 pp. 1-4 (Nov. 23, 2017).
Liu et al., "Structural Characterization and Relaxivity Study of a New Paramagnetic Mn(II) Complex of DTPA-BpABA," *Chinese Journal of Chemistry* 23 1012-1016 (2005).
Tei, et al., "Mn(II) complexes of novel hexadentate AAZTA-like chelators: a solution thermodynamics and relaxometric study," *Dalton Transaction.*, 40(9), 2025-2032 (2011).
Liao et al., "Synthesis and Evaluation of Neutral Gd(III), Mn(II) Complexes From DTPA-Bisamide Derivative as Potential MRI Contrast Agents," *Journal Homepage* http://www/tandonline.com/loi/lsrt20 ISSN: 1553-3174 (2015).
Zoltán et al., "Effect of the Nature of Donor Atoms on the Thermodynamic, Kinetic and Relaxation Properties of Mn(II) Complexes Formed With Some Trisubstituted 12-Membered Macrocyclic Ligands," Frontiers in Chemistry pp. 1-14 (2018).
Zoltán et al., "Physico-chemical properties of $Mn^{II}$ complexes formed with cis-and trans-DO2A: thermodynamic, electrochemical and kinetic studies," *Journal of Inorganic Biochemistry* 163 pp. 206-213 (2016).
Choppin, et al., Lanthanide(III) Complexation with Ligands as Possible Contrast Enhancing Agents for MRI, Inorganica Chimica Acta 252, 299-310 (1996).

\* cited by examiner

3,6,9, 15-TETRAAZA-BICYCLO [9.3.1]PENTADECA-1(14), 11(15), 12-TRIENE BASED COMPOUNDS AND THEIR APPLICATION AS LIGANDS OF ESSENTIAL METAL ION BASED MRI AND 52MN BASED PET CONTRAST AGENTS

Subject of the invention is new substituted 3,6,9,15-tetraaza-bicyclo[9.3.1]pentadeca-1(14),11(15),12-triene derivatives and their application as ligands of Mn(II), Fe(II), Fe(III), Co(II) and Ni(II) based MRI and $^{52}$Mn based PET contrast agents.

The invention is referring to new compounds and their applications.

One subject of the invention the compounds of the general formula (I):

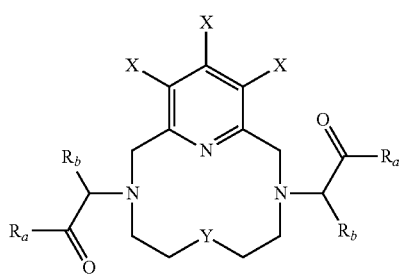

(I)

wherein
$R_a$ refers to —OH group or —NR$_3$R$_4$ group
and —NR$_3$R$_4$ group may refer to:
a) —NR$_3$R$_4$ with N atom in the ring means a ring of 4 to 7, that in certain cases may contain another heteroatom, and in specific cases the ring may be replaced with an aryl group (of 5 to 7 carbon atoms) substituted with —COOH, —OH, —OCH$_3$, —NO$_2$, —NH$_2$, —NCS, —NHS-activated ester, aryl (of 5 to 7 carbon atoms), or nitro-, amino- or isothiocyanate group, or
b) in the —NR$_3$R$_4$ group R$_3$ means a H atom, alkyl, aryl, nitroaryl, aminoaryl or isothiocyanate-aryl group (of 1 to 6 carbon atoms) and R$_4$ is a H atom, alkyl (of 1 to 6 carbon atoms) or —(CH$_2$)$_n$—COOH group, whereas n=1 to 10 integer, or
c) —NR$_3$R$_4$ group is one of the below groups:

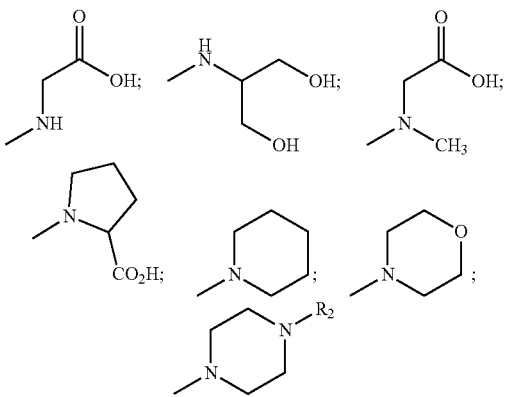

whereas R$_2$ is a H atom, carboxyl- or alkyl-carbonyl group (of 1 to 4 carbon atoms);

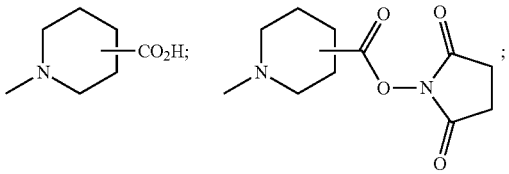

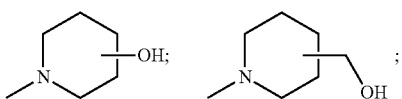

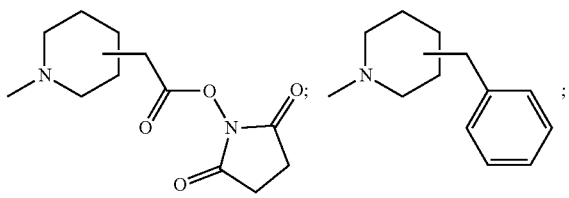

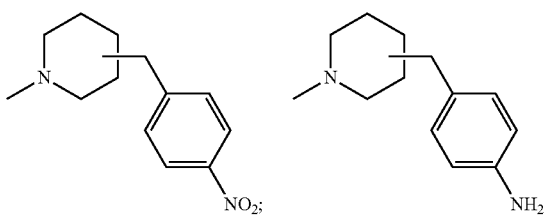

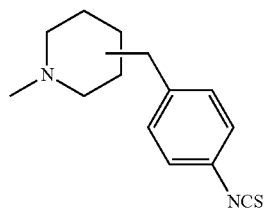

and
R$_b$ is a H atom or alkyl or aryl group (of 1 to 6 carbon atoms),
and
X means independently from one another H atom, —CH$_3$, —COOH, —OH, —OCH$_3$, alkoxy-(of 2 to 6 carbon atoms), —NO$_2$, —NH$_2$, —NCS, —NHS-activated ester, alkyl (of 2 to 12 carbon atoms) or aryl (of 5 to 7 carbon atoms) group, in certain cases the latter may be substituted with hydroxyl, hydroxyalkyl (of 1 to 6 carbon atoms), nitro, amino or isothiocyanate group; and Y means: —NH— or >NCH$_2$—Z group, whereas in the >NCH$_2$—Z group Z refers to one selected group of the below:
—C(O)NR$_3$R$_4$ group, in which —NR$_3$R$_4$ means as referred to above,

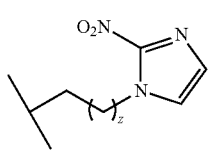

whereas z=0-18 integer,

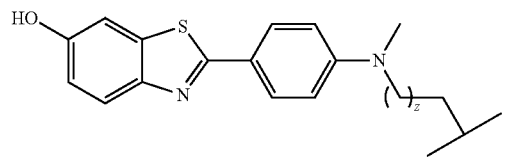

whereas z=0-18 integer,

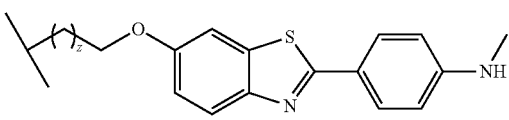

whereas z=0-18 integer,

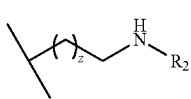

whereas z=0-18 integer and H atom, alkyl (of 1 to 6 carbon atoms) or —$(CH_2)_n$—COOH group, whereas n=1 to 10 integer, or,

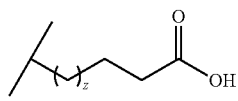

whereas z=0-18 integer,

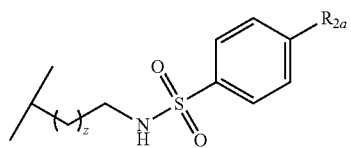

whereas z=0-18 integer and $R_{2a}$ refers to H atom, —$CH_3$, —$OCH_3$, or —$CF_3$ group,

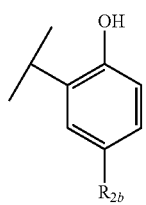

whereas $R_{2b}$ refers to H atom, —$CH_3$, —$OCH_3$, —$CF_3$, —COOH, —$COON(CO)_2(CH_2)_2$, —$NO_2$, —$NH_2$ or —NCS— group,

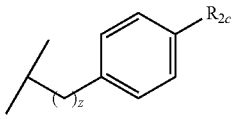

whereas z=0-18 integer and $R_{2c}$ refers to H atom, —$NO_2$, —$NH_2$ or —NCS— group,

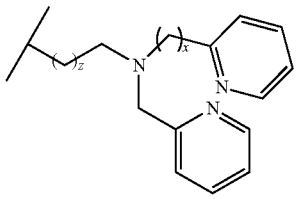

whereas z=0-18, and x=1-5 integer,

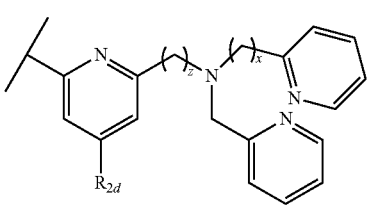

wherein z=1-5, and x=1-5 integer, $R_{2d}$ refers to H atom, —$CH_3$, —$OCH_3$, —$CF_3$, —COOH, —$COON(CO)_2(CH_2)_2$, —$NO_2$, —$NH_2$ or —NCS group, Mn(II), Fe(II), Fe(III), Co(II), and Ni(II) complexes of compounds of general formula (I) can be applied beneficially in MRI diagnostics and $^{52}$Mn-based PET imaging as contrast agents.

The majority of contrast agents applied in MRI diagnostics are complexes of paramagnetic Gd(III) ion formed with DTPA and DOTA and its derivatives. An important disadvantage of Gd(III) containing contrast agents is the toxicity of Gd(III) ion, therefore very strict requirements shall be fulfilled for their application as contrast agent. Nephrogenic Systemic Fibrosis (NSF) discovered in the beginning of the 21$^{st}$ century and associated with the use of Gd(III) containing contrast agents for patients with severe renal disease pointed out that problems may arise due to the use of toxic Gd(III) even in spite of the strict requirement system. Furthermore, the negative outcome of using high quantities of Gd(III) based contrast agents, e.g. gadolinium accumulating in surface waters and coming from clinical waste waters also poses an increasing problem.

The only contrast agent without Gd(III) used in practice was Mangafodipir (Tesalscan) with Mn(II) ion as the central paramagnetic ion, but this was withdrawn from the market some years ago.

One possibility to replace Gd(III) containing compounds is the use complexes of essential paramagnetic ions (such as Mn(II), Fe(II), Fe(III)) as contrast agents, since Mn(II) ion is an essential metal ion, thus appropriate routes for elimination of Mn(II) ion are available in living organisms.

Mangafodipir mentioned above can be applied in liver diagnostics due to the different Mn(II) uptake of the healthy and abnormal hepatocytes. In case of Mangafodipir contrast agent, the Mn(II) ions releasing after dissociation of the complex are absorbed possibly owing to low kinetic inertness of the given complex. At the same time, however, publications are available to support, that despite the endogenic nature of the Mn(II) ion, extended expositions and high doses may cause neurodegenerative changes with Parkinson-like symptoms. Therefore it is more safe to use Mn(II), Fe(II), Fe(III) ion containing contrast agents (complexes) not dissociating or dissociating only at a very small extent while the complex is excreted form the body. The kinetic inertness of Co(II) and Ni(II) ion based contrast agents are also important for very similar reasons.

During the research of Mn(II) ion based contrast agent, synthesis of a macrocycle based complexes really applicable as contrast agents in Magnetic Resonance Imaging (MRI) have not been succeeded yet. It is obviously due to the small contrast increasing effect of complexes obviously caused by the lack of water molecule bound directly to the metal ion. To solve this problem, we managed to synthesize macrocyclic ligands, the Mn(II) complexes of which preserve the good equilibrium and kinetic properties, while their relaxation properties fulfil the requirements related to MRI contrast agents (e.g. water molecule is present in the internal coordination sphere). In addition, we also recommend a list of other compounds designed as intelligent contrast agents, agents capable to respond with changes in their relaxation effect to the changes in the environment, e.g. respond to pH change, or change in $Zn^{2+}$ ion concentration, able to indicate lack of oxygen (hypoxia) or bind to the HSA.

Together with other documents, the published EP 130934 document describes Mn(II) ion containing contrast agents and substituted tetraacetic-acid-bis(amide) type ligands suitable for the preparation of the mentioned contrast agents, describing trans-1,2-cyclohexanediamine-tetraacetic acid (CDTA)-bis(amide) derivatives) and their Mn(II), Fe(II), Fe(III), Co(II), and Ni(II) complexes.

The published EP 263059 document provides additional similar compounds as derivatives of the trans-1,2-cyclohexanediamine-tetraacetic acid-bismethyl-amide and bis(3-oxa-pentamethylene)-carboxamide.

The published US 2011/0092806 document describes 'chelate-linker-biovector' type associates for application in diagnostic imaging having DPTA, DOTA, NOTA, DO3A and PCTA basic structure or their derivatives.

The WO 2011/073371 international publication refers to substituted 3,6,9,15-tetraazabicyclo[9.3.1]pentadecatriene derivatives and the Mn(II) complexes of the same carrying acetic acid ester group on the basic structure.

In our research, the goal was to develop Mn(II), Fe(II), Fe(III), Co(II) and Ni(II) ion based complexes of high relaxivity and low reactivity to apply as MRI contrast agents and $^{52}$Mn-based PET diagnostics.

In our experiments, the 3,6,9,15-tetraazabicyclo[9.3.1] pentadeca-1(14),11(15),12-triene macrocycle and its derivatives were found favourable as complex forming agent of new type contrast agents.

Preparation of compounds of the invention is shown in the following examples.

EXAMPLE 1

Synthesis of tPC2AM$^{Pyp}$ a.) 2-bromo-1-(piperidine-1-yl)ethanone: Bromoacetyl bromide (3.56 g, 17.6 mmol, 1.55 ml, 1.5 equivalent), dry $CH_2Cl_2$ (50 ml) and $K_3PO_4$ (6.41 g, 30.2 mmol, 2.5 equ.) was mixed in a flask of 250 ml under $N_2$ atmosphere. Piperidine (1.00 g, 11.7 mmol, 1.0 equivalent) was dissolved in dry $CH_2Cl_2$ (20 ml) and was added dropwise to dichloromethane solution of bromoacetyl bromide at 0° C. in 30 minutes, then the reaction mixture was stirred for additional 12 hours at room temperature under $N_2$ atmosphere before the aqueous HCl solution (0.5 M, 30 ml) was added to the reaction mixture. After the addition of HCl solution, the reaction mixture was stirred for additional 5 minutes, then the two phases were separated using a separatory funnel. The aqueous phase was washed with $CH_2Cl_2$ (1×15 ml) and then the unified organic phases were washed with $KHCO_3$ solution (2×30 ml, 10 m/m %) and saturated NaCl solution (1×30 ml). The organic phase was dried with $MgSO_4$, then dichloromethane was evaporated at reduced pressure, and the crude product was stored at −20° C. until further use. Yield: 1.73 g (70%).

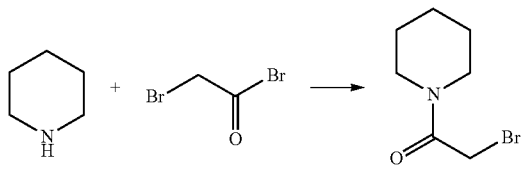

$^1$H NMR [360 MHz, CDCl$_3$] δ 1.59 (2H, m, (CH$_2$) ring), 1.67 (4H, m, (CH$_2$) ring), 3.45 (2H, t, (CH$_2$) ring), 3.59 (2H, t, (CH$_2$) ring), 3.87 (2H, s, (CH$_2$)), $^{13}$C NMR [100 MHz, CDCl$_3$] δ 25.4 2pcs CH$_2$ ring; 26.0 CH$_2$ ring; 27.2 CH$_2$Br; 44.2 2pcs CH$_2$ ring; 169.5 C(=O);

b.) tPC2AM$^{Pyp}$ synthesis: The 2-bromo-1-(piperidin-1-yl) ethanone obtained as described above (0.22 g, 1.06 mmol, 2.2 equivalent) was dissolved in dry acetonitrile and added dropwise to the acetonitrile solution (30 ml) of 3,6,9,15-tetraazabicyclo[9.3.1]pentadeca-1(14),11(15),12-triene (0.10 g, 0.48 mmol, 1 equivalent) and $K_2CO_3$ (0.2 g, 1.44 mmol, 3 equivalent) at room temperature within 30 minutes. Then the reaction mixture was refluxed in $N_2$ atmosphere for 24 hours. After 24 hours, $K_2CO_3$ was filtered from the hot solution, and acetonitrile was evaporated at reduced pressure. The obtained crude product was purified with HPLC (Luna 10u-Prep C18(2) 100A (250×21.20 mm; 10 μm) column), ACN:H$_2$O/TFA-t was applied as eluent [ACN: acetonitrile; TFA: trifluoroacetic acid]. TFA was contained only in water in 0.005 M concentration. Yield: 0.14 g (64%).

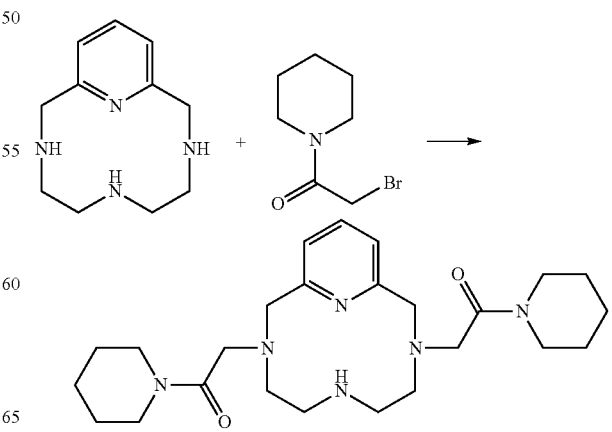

NMR [360 MHz, D$_2$O] δ 1.40-1.70 (12H, m, (6pcs CH$_2$)), 3.30 (8H, m, (4pcs CH$_2$)), 3.40-3.55 (8H, m, (4pcs CH$_2$)), 4.32 (4H, s, (2pcs CH$_2$)), 4.62 (4H, s, (2pcs CH$_2$)), 7.63 (2H, d, (CH) aromatic), 8.16 (1H, t, (CH) aromatic);

$^{13}$C NMR [100 MHz, D$_2$O] δ 23.5 2pcs CH$_2$; 25.2 2pcs CH$_2$; 25.6 2pcs CH$_2$; 43.7 2pcs CH$_2$; 44.8 2pcs CH$_2$; 45.9 2pcs CH$_2$; 53.0 2pcs CH$_2$; 57.5 2pcs CH$_2$; 58.5 2pcs CH$_2$; 123.6 2pcs CH aromatic; 144.3 CH aromatic; 153.0 2pc C aromatic; 167.7 2pcs C(=O); MS (ESI) m/z 457.520(M+H)$^+$100%; 479.50(M+Na)$^+$8%;

IR: 1636 cM$^{-1}$ (>C=O); 2162, 2010 (Aromatic >C=C)

EXAMPLE 2

Synthesis of tPC2AM$^{Pro}$ a.) Tert-butyl 1-(2-bromoacetyl)pyrrolidine-2-carboxylate: Bromoacetyl bromide (1.44 g, 7.2 mmol, 0.63 ml, 1.5 equivalent), dry CH$_2$Cl$_2$ (30 ml) and K$_3$PO$_4$ (2.55 g, 12.0 mmol, 2.5 equ.) was mixed in a flask of 250 ml and stirred under N$_2$ atmosphere. D-proline tert-butyl ester hydrochloride (1.00 g, 4.8 mmol, 1.0 equivalent) was dissolved in dry CH$_2$Cl$_2$ (20 ml) and was added dropwise to dichloromethane solution of bromoacetyl bromide at 0° C. in 30 minutes, then the reaction mixture was stirred for additional 12 hours at room temperature under N$_2$ atmosphere before the aqueous HCl solution (0.5 M, 20 ml) was added to the reaction mixture. After the addition of HCl solution, the reaction mixture was stirred for additional 5 minutes, then the two phases were separated using a separatory funnel. The aqueous phase was washed with CH$_2$Cl$_2$ (1×10 ml) and then the unified organic phases were washed with KHCO$_3$ solution (2×20 ml, 10 m/m %) and saturated NaCl solution (1×20 ml). The organic phase was dried with MgSO$_4$, then dichloromethane was evaporated at reduced pressure, and the crude product was stored at −20° C. until further use. Yield: 1.05 g (75%).

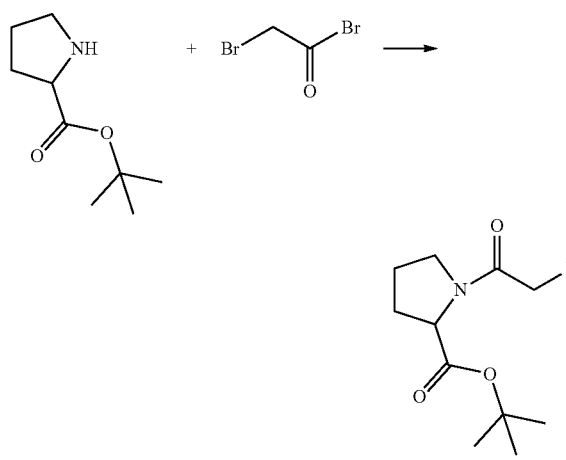

$^1$H NMR [360 MHz, CDCl$_3$] δ 1.60 (9H, s, (CH$_3$)), 2.15 (2H, m, (CH$_2$) ring), 2.43 (2H, m, (CH$_2$)ring), 3.72 (2H, m, (CH$_2$) ring), 4.00 (2H, s, (CH$_2$)), 4.55 (1H, m, (CH) ring);

$^{13}$C NMR [100 MHz, CDCl$_3$] δ25.0 CH$_2$ ring; 27.0 CH$_2$Br; 28.0 (3C CH$_3$); 29.2 CH$_2$ ring; 47.5 CH$_2$ ring; 60.2 CH ring; 81.8 CH t-butyl; 165.2 C(=O); 170.9 C(=O);

b.) tPC2AM$^{Pro}$ synthesis: The tert-butyl 1-(2-bromoacetyl)pyrrolidine-2-carboxylate obtained as described above (0.32 g, 1.08 mmol, 2.2 equivalent) was dissolved in dry acetonitrile (20 ml) and added dropwise to the acetonitrile solution of 3,6,9,15-tetraazabicyclo[9.3.1]pentadeca-1(14),11(15),12-triene (0.10 g, 0.49 mmol, 1 equivalent) and K$_2$CO$_3$ (0.2 g, 1.47 mmol, 3 equivalent) at room temperature within 30 minutes. Then the reaction mixture was refluxed in N$_2$ atmosphere for 24 hours. After 24 hours, K$_2$CO$_3$ was filtered from the hot solution, and acetonitrile was evaporated at reduced pressure. The obtained yellowish oil was dissolved in CH$_2$Cl$_2$ (10 ml), then trifluoroacetic acid is added to it (0.23 ml, 6 equivalent) and the reaction mixture was refluxed for 24 hours. The obtained crude product was purified with HPLC (Luna 10u-Prep C18(2) 100A (250× 21.20 mm; 10 μm) column), ACN:H$_2$O/TFA-t was applied as eluent [ACN: acetonitrile; TFA: trifluoroacetic acid]. TFA was contained only in water in 0.005 M concentration. Yield: 0.13 g (52%).

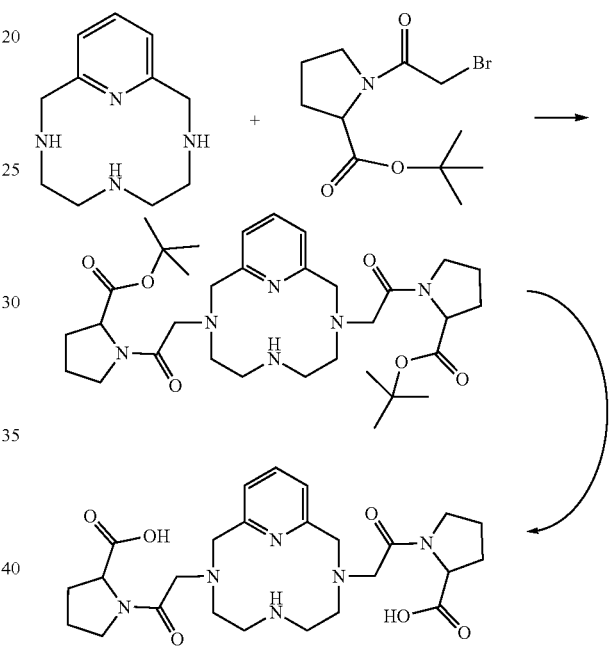

$^1$H NMR [360 MHz, D$_2$O] δ 2.00 (6H, m, (CH$_2$)), 2.28 (2H, m, (CH$_2$)), 3.16 (2H, m, (CH$_2$)), 3.52 (10H, m, (CH$_2$)), 4.45 (8H, m, (CH$_2$)), 4.53 (2H, m, (CH)), 7.37 (1H, d, (CH) aromatic), 7.44 (1H, d, (CH) aromatic) 7.92 (1H, t, (CH) aromatic);

$^{13}$C NMR [100 MHz, D$_2$O] δ 24.3 2 pcs CH$_2$; 28.9 2 pcs CH$_2$; 46.5 2pcs CH$_2$; 51.4 2pcs CH$_2$; 56.1 2pcs CH$_2$, 59.6 2pcs CH$_2$; 60.2 2pcs CH; 121.8 1pcs CH aromatic; 122.7 1pc CH aromatic; 140.0 1 pc CH aromatic; 149.2 1pc C aromatic; 149.7 1 pc C aromatic; 163.8 2pcs C(=O); 171.5 2pcs C (COOH);

MS (ESI) m/z 517.67(M+H)$^+$100%; 539.67(M+Na)$^+$35%;
IR: 1721, 1652 cm$^-$ (>C=O); 2158, 2025 (Aromatic >C=C)

EXAMPLE 3

Synthesis of tPC2AM$^{Morf}$

The commercially available 4-(bromoacetyl)morpholine (0.22 g, 1.06 mmol, 2.2 equivalent) was dissolved in dry acetonitrile, then added dropwise to the acetonitrile suspension (30 ml) of 3,6,9,15-tetraazabicyclo[9.3.1]pentadeca-1

(14),11(15),12-triene (0.10 g, 0.48 mmol, 1 equivalent) and K₂CO₃ (0.2 g, 1.44 mmol, 3 equivalent) at room temperature within 30 minutes. Then the reaction mixture was refluxed in N₂ atmosphere for 24 hours. After 24 hours, K₂CO₃ was filtered from the hot solution, and the solvent was evaporated at reduced pressure. The obtained crude product was purified with HPLC (Luna 10u-Prep C18(2) 100A (250× 21.20 mm; 10 μm) column), ACN:H₂O/TFA was applied as eluent [ACN: acetonitrile; TFA: trifluoroacetic acid]. TFA was contained only in water in 0.005 M concentration. Yield: 0.11 g (50%).

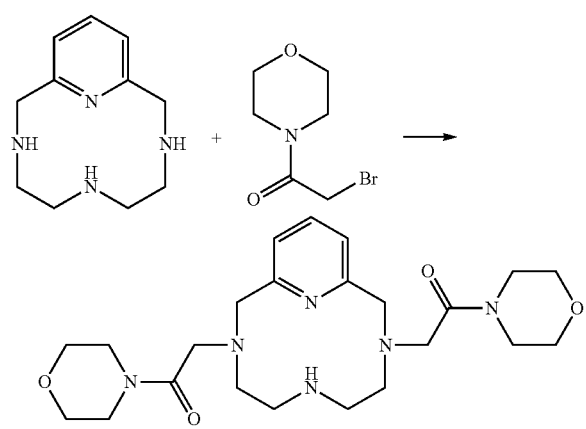

¹H NMR [360 MHz, D₂O] δ 2.40-2.66 (8H, m, (4pcs CH₂)), 3.32 (4H, s, (2pcs CH₂)), 3.46-3.71 (8H, m, (4pcs CH₂)), 4.10 (4H, s, (2pcs CH₂)), 7.61 (2H, d, (CH) aromatic), 8.12 (1H, t, (CH) aromatic);

¹³C NMR [100 MHz, D₂O] δ 44.5 2pcs CH₂; 48.8 4pcs CH₂; 56.6 2pcs CH₂; 59.8 2pcs CH₂; 69.2 2pcs CH₂; 118.3 2pcs C aromatic; 133.2 1pcs C aromatic; 159.0 2pcs C aromatic; 168.0 2pcs C(=O)

EXAMPLE 4

Synthesis of tPC2AM$^{PipAc}$

The commercially available 1-acetyl-4-(bromoacetyl) morpholine piperazine (0.26 g, 1.04 mmol, 2.15 equivalent) was dissolved in dry acetonitrile (5.00 cm³), then added dropwise to the acetonitrile suspension (30 ml) of 3,6,9,15-tetraazabicyclo[9.3.1]pentadeca-1(14),11(15),12-triene (0.10 g, 0.48 mmol, 1 equivalent) and K₂CO₃ (0.2 g, 1.44 mmol, 3 equivalent) at room temperature within 30 minutes. Then the reaction mixture was refluxed in N₂ atmosphere for 24 hours. After 24 hours, K₂CO₃ was filtered from the hot solution, and the filtrate was evaporated at reduced pressure. The obtained crude product was purified with HPLC (Luna 10u-Prep C18(2) 100A (250×21.20 mm; 10 μm) column), ACN:H₂O/TFA was applied as eluent [ACN: acetonitrile; TFA: trifluoroacetic acid]. TFA was contained only in water in 0.005 M concentration. Yield: 0.12 g (46%).

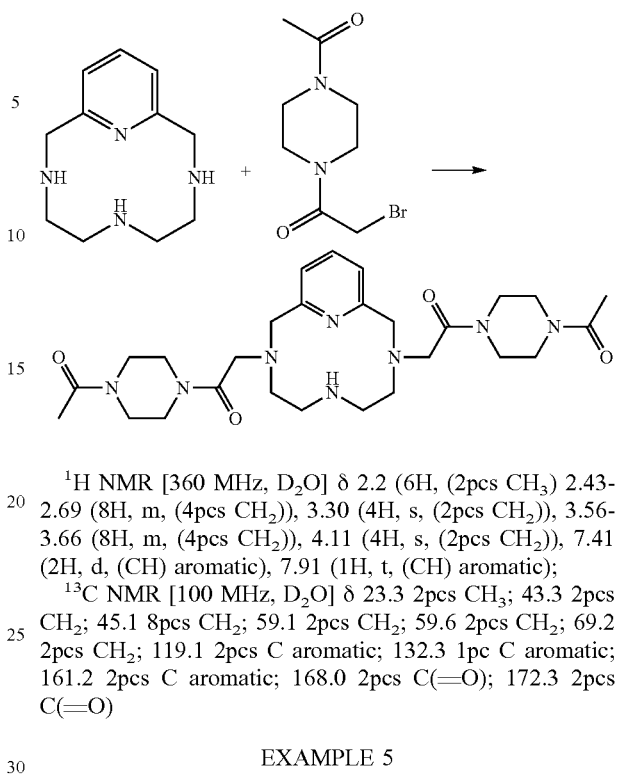

¹H NMR [360 MHz, D₂O] δ 2.2 (6H, (2pcs CH₃) 2.43-2.69 (8H, m, (4pcs CH₂)), 3.30 (4H, s, (2pcs CH₂)), 3.56-3.66 (8H, m, (4pcs CH₂)), 4.11 (4H, s, (2pcs CH₂)), 7.41 (2H, d, (CH) aromatic), 7.91 (1H, t, (CH) aromatic);

¹³C NMR [100 MHz, D₂O] δ 23.3 2pcs CH₃; 43.3 2pcs CH₂; 45.1 8pcs CH₂; 59.1 2pcs CH₂; 59.6 2pcs CH₂; 69.2 2pcs CH₂; 119.1 2pcs C aromatic; 132.3 1pc C aromatic; 161.2 2pcs C aromatic; 168.0 2pcs C(=O); 172.3 2pcs C(=O)

EXAMPLE 5

Synthesis of tPC2AM$^{Sar}$ a.) N-(bromoacetyl)sarcosine tert-butyl ester: Bromoacetyl bromide (3.56 g, 17.6 mmol, 1.55 ml, 1.5 equivalent), dry CH₂Cl₂ (50 ml) and K₃PO₄ (6.41 g, 30.2 mmol, 2.5 equ.) was mixed in a flask of 250 ml under N₂ atmosphere. Sarcosine tert-butyl ester (1.7 g, 11.7 mmol, 1.0 equivalent) was dissolved in dry CH₂Cl₂ (20 ml) and was added dropwise to dichloromethane solution of bromoacetyl bromide at 0° C. in 30 minutes, then the reaction mixture was stirred for additional 12 hours at room temperature under N₂ atmosphere before the aqueous HCl solution (0.5 M, 30 ml) was added to the reaction mixture. After the addition of HCl solution, the reaction mixture was stirred for additional 5 minutes, then the two phases were separated using a separatory funnel. The aqueous phase was washed with CH₂Cl₂ (1×15 ml) and then the unified organic phases were washed with KHCO₃ solution (2×30 ml, 10 m/m %) and saturated NaCl solution (1×30 ml). The organic phase was dried with MgSO⁴, then dichloromethane was evaporated at reduced pressure, and the crude product was stored at −20° C. until further use. Yield: 2.01 g (65%).

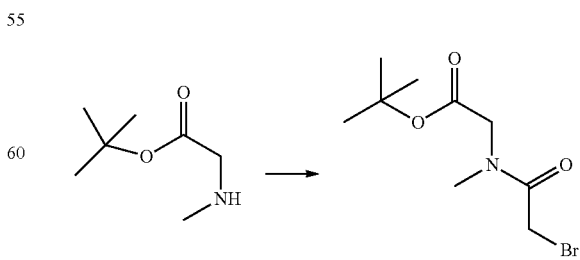

¹H NMR [360 MHz, CDCl₃] δ 1.6 (9H, s, CH₃) 2.8 (3H, s, CH₃), 4.01 (2H, s, CH₂), 4.4 (2H, s, CH₂)

b). Synthesis of tPC2AM$^{Sar}$: The N-(bromoacetyl)sarcosine tert-butyl ester obtained as described above (0.29 g, 1.08 mmol, 2.2 equivalent) was dissolved in dry acetonitrile (20 ml) and added dropwise to the acetonitrile solution of 3,6,9,15-tetraazabicyclo[9.3.1]pentadeca-1(14),11(15),12-triene (0.10 g, 0.49 mmol, 1 equivalent) and $K_2CO_3$ (0.2 g, 1.47 mmol, 3 equivalent) at room temperature within 30 minutes. Then the reaction mixture was refluxed in N2 atmosphere for 24 hours. After 24 hours, $K_2CO_3$ was filtered from the hot solution, and acetonitrile was evaporated at reduced pressure. The obtained yellowish oil was dissolved in $CH_2Cl_2$ (10 ml), then trifluoroacetic acid is added to it (0.25 ml, 6 equivalent) and the reaction mixture was refluxed for 24 hours. The obtained crude product was purified with HPLC (Luna 10u-Prep C18(2) 100A (250×21.20 mm; 10 μm) column), ACN:$H_2O$/TFA-t was applied as eluent [ACN: acetonitrile; TFA: trifluoroacetic acid]. TFA was contained only in water in 0.005 M concentration. Yield: 0.14 g (60%). 1H NMR [360 MHz, D2O] δ 7.91 (1H, t, aromatic), 7.35 (2H, d, aromatic) 4.97 (4H, s, $CH_2$) 4.12 (4H, s, $CH_2$) 3.66 (6H, s, $CH_3$) 3.21 (4H, s, $CH_2$) 2.67 (4H, m, $CH_2$) 2.55 (4H, m, $CH_2$).

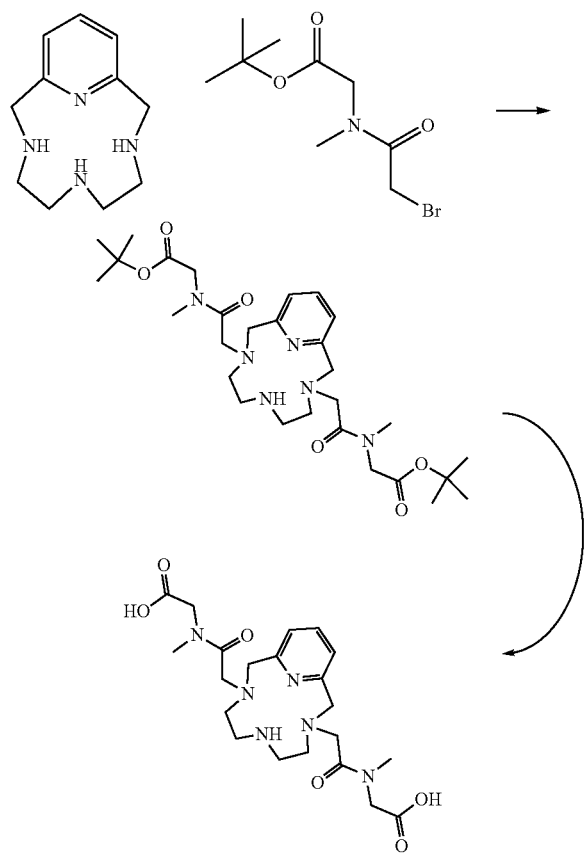

EXAMPLE 6

Synthesis of tPC2AM$^{PypCOOH}$ a.) N-(bromoacetyl)piperidine-4-carboxylic acid tert-butyl ester: Bromoacetyl bromide (3.56 g, 17.6 mmol, 1.55 ml, 1.5 equivalent), dry $CH_2Cl_2$ (50 ml) and $K_3PO_4$ (6.41 g, 30.2 mmol, 2.5 equivalent) was mixed in a flask of 250 ml under $N_2$ atmosphere. Piperidine tert-butyl ester (2.2 g, 11.7 mmol, 1.0 equivalent) was dissolved in dry $CH_2Cl_2$ (20 ml) and was added dropwise to dichloromethane solution of bromoacetyl bromide at 0° C. in 30 minutes, then the reaction mixture was stirred for additional 12 hours at room temperature under $N_2$ atmosphere before the aqueous HCl solution (0.5 M, 30 ml) was added to the reaction mixture. After the addition of HCl solution, the reaction mixture was stirred for additional 5 minutes, then the two phases were separated using a separatory funnel. The aqueous phase was washed with $CH_2Cl_2$ (1×15 ml) and then the unified organic phases were washed with $KHCO_3$ solution (2×30 ml, 10 m/m %) and saturated NaCl solution (1×30 ml). The organic phase was dried with $MgSO_4$, then dichloromethane was evaporated at reduced pressure, and the crude product was stored at −20° C. until further use. Yield: 2.1 g (59%).

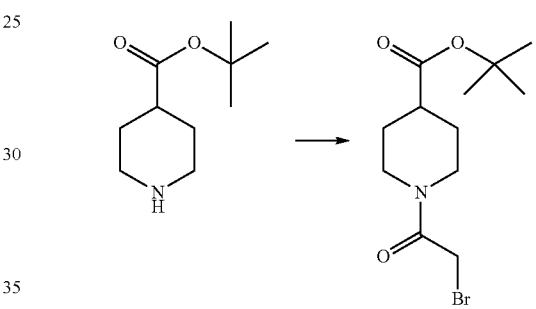

$^1$H NMR [360 MHz, $CDCl_3$] δ 1.50 (9H, s, $CH_3$) 2.50 (1H, s, CH), 4.01 (2H, s, ($CH_2$), 3.5-1.6 (811, m, $CH_2$), 4.31 (2H, s, $CH_2$)

b). preparation of tPC2AMPypCOOH: The N-(bromoacetyl)piperidine tert-butyl ester obtained as described above (0.33 g, 1.08 mmol, 2.2 equivalent) was dissolved in dry acetonitrile (20 ml) and added dropwise to the acetonitrile solution of 3,6,9,15-tetraazabicyclo[9.3.1]pentadeca-1(14),11(15),12-triene (0.10 g, 0.49 mmol, 1 equivalent) and $K_2CO_3$ (0.2 g, 1.47 mmol, 3 equivalent) at room temperature within 30 minutes. Then the reaction mixture was refluxed in $N_2$ atmosphere for 24 hours. After 24 hours, $K_2CO_3$ was filtered from the hot solution, and acetonitrile was evaporated at reduced pressure. The obtained yellowish oil was dissolved in $CH_2Cl_2$ (10 ml), then trifluoroacetic acid is added to it (0.25 ml, 6 equivalent) and the reaction mixture was refluxed for 24 hours. The obtained crude product was purified with HPLC (Luna 10u-Prep C18(2) 100A (250×21.20 mm; 10 μm) column), ACN:$H_2O$/TFA-t was applied as eluent [ACN: acetonitrile; TFA: trifluoroacetic acid]. TFA was contained only in water in 0.005 M concentration. Yield: 0.19 g (70%). $^1$H NMR [360 MHz, $D_2O$] δ 7.91 (1H, t, aromatic), 7.33 (2H, d, aromatic) 4.11 (4H, s, $CH_2$) 3.75-3.22 (8H, m, $CH_2$) 3.29 (4H, s, $CH_2$) 2.67 (4H, m, $CH_2$) 2.44 (4H, m,) 2.44 (2H, m, CH) 1.96-1.44 (8H, m, $CH_2$)

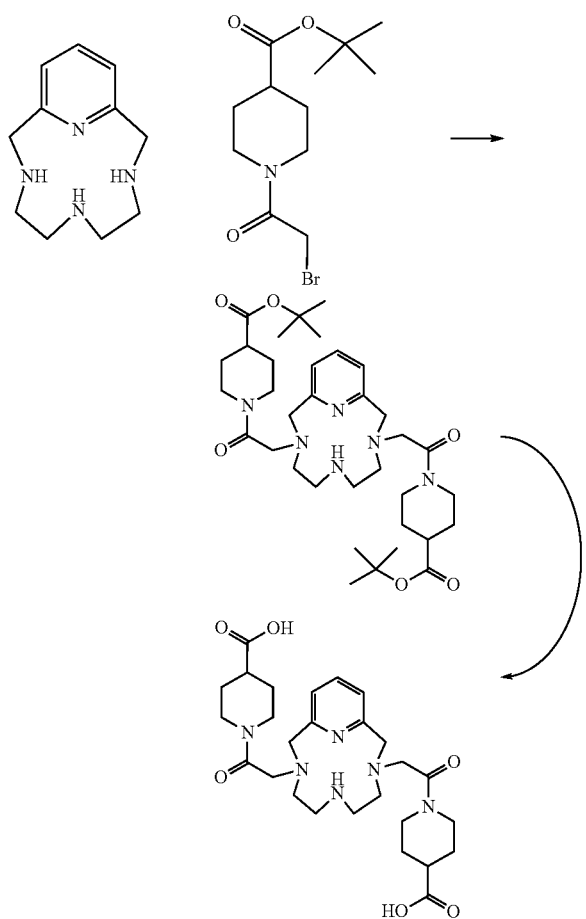

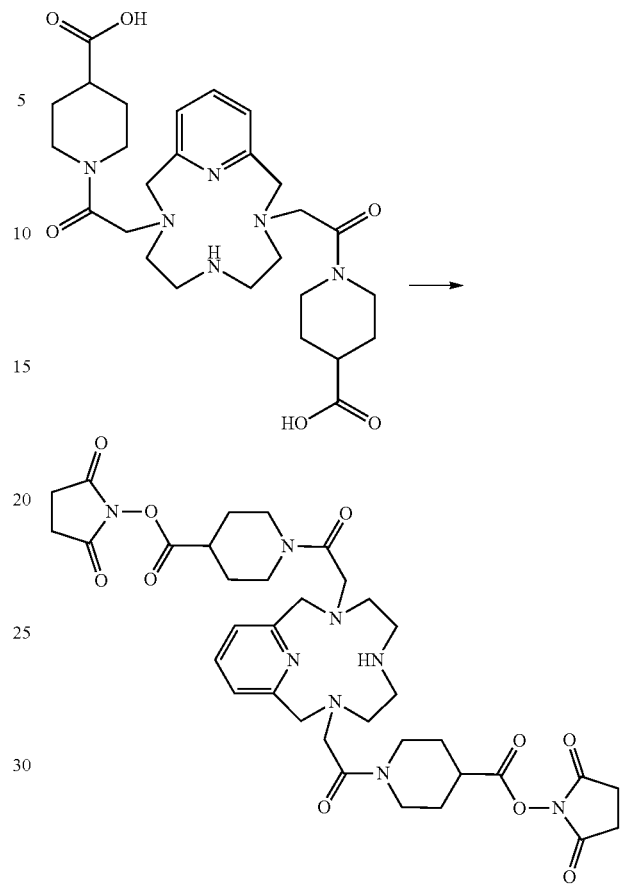

EXAMPLE 7

Synthesis of tPC2AM$^{PypCOONHS}$ c). tPC2AMi$^{PypCOONHS}$ preparation: The tPC2AM$^{PypCOOH}$ (0.20 g, 0.37 mmol, 1.0 equivalent) obtained as described above was dissolved in dry DMF, then DCC (0.15 g, 0.74 mmol, 2 equ.) was added at room temperature and the reaction mixture was stirred at room temperature for 2 hours. Then NHS (N-Hydroxysuccinimide) (0.085 g, 0.74 mmol, 2 equ.) was added and the reaction mixture was stirred for additional 20 hours. When the reaction time was elapsed, the precipitate was filtered, and the filtrate was evaporated at reduced pressure. The obtained crude product was purified with HPLC (Luna 10u-Prep C18(2) 100A (250×21.20 mm; 10 μm) column), ACN:H$_2$O/TFA-t was applied as eluent [ACN: acetonitrile; TFA: trifluoroacetic acid]. TFA was contained only in water in 0.005 M concentration. Yield: 0.17 g (63%). $^1$H NMR [360 MHz, D$_2$O] δ 7.92 (1H, t, aromatic), 7.31 (2H, d, aromatic) 4.04 (4H, s, CH$_2$) 3.59-3.10 (8H, m, CH$_2$) 3.35 (4H, s, CH$_2$) 2.71 (4H, m, CH$_2$) 2.60 (8H, s, CH$_2$) 2.37 (4H, m, CH$_2$) 2.34 (2H, m, CH) 1.90-1.59 (8H, m, CH$_2$).

EXAMPLE 8

Synthesis of tPC2AM$^{PypCH2OH}$ a.) N-bromoacetyl-4-hydroxymethyl piperidine: Bromoacetyl bromide (3.56 g, 17.6 mmol, 1.55 ml, 1.5 equivalent), dry CH$_2$Cl$_2$ (50 ml) and K$_3$PO$_4$ (6.41 g, 30.2 mmol, 2.5 equ.) was mixed in a flask of 250 ml under N$_2$ atmosphere. 4-hydroxymethyl piperidine (1.34 g, 11.7 mmol, 1.0 equivalent) was dissolved in dry CH$_2$Cl$_2$ (20 ml) and was added dropwise to dichloromethane solution of bromoacetyl bromide at 0° C. in 30 minutes, then the reaction mixture was stirred for additional 12 hours at room temperature under N$_2$ atmosphere before the aqueous HCl solution (0.5 M, 30 ml) was added to the reaction mixture. After the addition of HCl solution, the reaction mixture was stirred for additional 5 minutes, then the two phases were separated using a separatory funnel. The aqueous phase was washed with CH$_2$Cl$_2$ (1×15 ml) and then the unified organic phases were washed with KHCO$_3$ solution (2×30 ml, 10 m/m %) and saturated NaCl solution (1×30 ml). The organic phase was dried with MgSO$_4$, then dichloromethane was evaporated at reduced pressure, and the crude product was stored at −20° C. until further use. Yield: 1.85 g (67%).

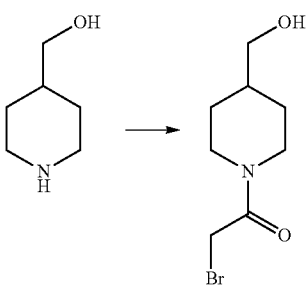 [SMILES: OCC1CCNCC1 ; O=C(CBr)N1CCC(CO)CC1]

¹H NMR [360 MHz, CDCl₃] δ 1.61 (1H, m, CH) 1.71-1.30 (8H, m, CH₂), 3.52 (2H, m, (CH₂), 4.21 (2H, s, CH₂)

b.) Synthesis of tPC2AM$^{PypCH2OH}$: The N-bromoacetyl-4-hydromethyl piperidine obtained as described above (0.29 g, 1.23 mmol, 2.5 equivalent) was dissolved in dry acetonitrile and added dropwise to the acetonitrile solution (30 ml) of (0.10 g, 0.49 mmol, 1 equivalent) and K₂CO₃ (0.2 g, 1.47 mmol, 3 equivalent) at room temperature within 30 minutes. Then the reaction mixture was refluxed in N2 atmosphere for 24 hours. After 24 hours, K₂CO₃ was filtered from the hot solution, and acetonitrile was evaporated at reduced pressure. The obtained crude product was purified with HPLC (Luna 10u-Prep C18(2) 100A (250×21.20 mm; 10 μm) column), ACN:H₂O/TFA-t was applied as eluent [ACN: acetonitrile; TFA: trifluoroacetic acid]. TFA was contained only in water in 0.005 M concentration. Yield: 0.17 g (69%).

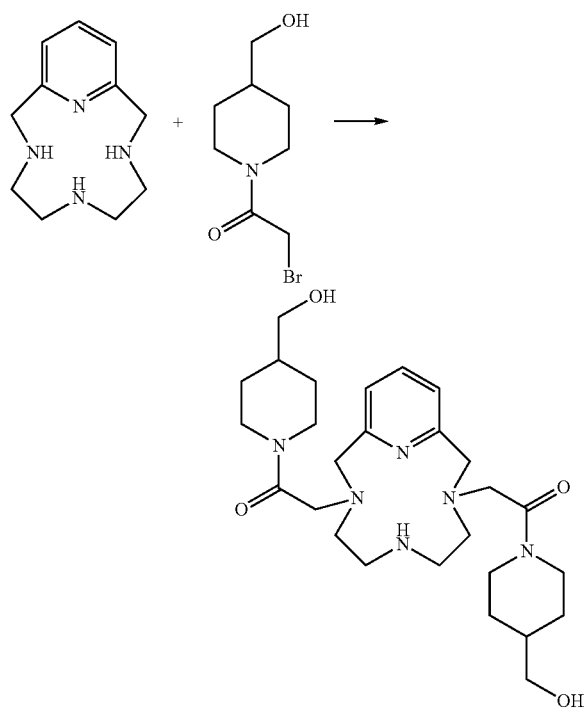

¹H NMR [360 MHz, D₂O] δ 8.05 (1H, t, aromatic), 7.32 (2H, d, aromatic) 4.10 (4H, s, CH₂) 3.62 (4H, d, CH₂) 3.55 (4H, m, CH₂) 3.49-3.21 (8H, m, CH₂) 3.38 (4H, s, CH₂) 2.61 (4H, t, CH₂), 1.63-1.33 (8H, m, CH₂) 1.61 (2H, m, CH)

EXAMPLE 9

Manufacture of tPC2AM$^{PypBn}$ a.) N-bromoacetyl-4-benzylpiperidine: Bromoacetyl bromide (3.56 g, 17.6 mmol, 1.55 ml, 1.5 equivalent), dry CH₂Cl₂ (50 ml) and K₃PO₄ (6.41 g, 30.2 mmol, 2.5 equ.) was mixed in a flask of 250 ml under N₂ atmosphere. 4-benzylpiperidine (2.05 g, 11.7 mmol, 1.0 equivalent) was dissolved in dry CH₂Cl₂ (20 ml) and was added dropwise to dichloromethane solution of bromoacetyl bromide at 0° C. in 30 minutes, then the reaction mixture was stirred for additional 12 hours at room temperature under N₂ atmosphere before the aqueous HCl solution (0.5 M, 30 ml) was added to the reaction mixture. After the addition of HCl solution, the reaction mixture was stirred for additional 5 minutes, then the two phases were separated using a separatory funnel. The aqueous phase was washed with CH₂Cl₂ (1×15 ml) and then the unified organic phases were washed with KHCO₃ solution (2×30 ml, 10 m/m %) and saturated NaCl solution (1×30 ml). The organic phase was dried with MgSO₄, then dichloromethane was evaporated at reduced pressure, and the crude product was stored at −20° C. until further use. Yield: 1.85 g (67%).

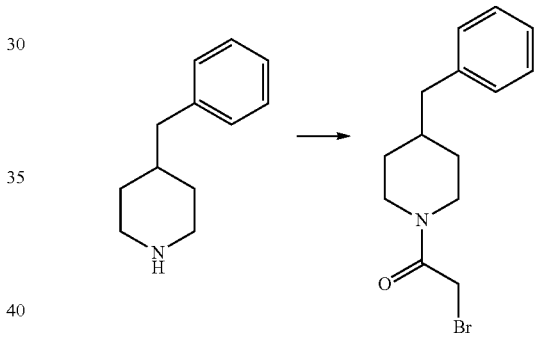

¹H NMR [360 MHz, CDCl₃] δ 1.91 (1H, m, CH) 1.69-1.24 (8H, m, CH₂) 2.66 (2H, m, CH₂) 4.23 (2H, s, (CH₂), 7.05-7.33 (5H, m, aromatic)

b.) Synthesis of tPC2AM$^{PypBn}$: The N-bromoacetyl-4-benzylpiperidine obtained as described above (0.32 g, 1.08 mmol, 2.2 equivalent) was dissolved in dry acetonitrile and added dropwise to the acetonitrile solution (30 ml) of 3,6,9,15-tetraazabicyclo[9.3.1]pentadeca-1 (14),11 (15),12-triene (0.10 g, 0.49 mmol, 1 equivalent) and K₂CO₃ (0.2 g, 1.47 mmol, 3 equivalent) at room temperature within 30 minutes. Then the reaction mixture was refluxed in N₂ atmosphere for 24 hours. After 24 hours, K₂CO₃ was filtered from the hot solution, and acetonitrile was evaporated at reduced pressure. The obtained crude product was purified with HPLC (Luna 10u-Prep C18(2) 100A (250×21.20 mm; 10 μm) column), ACN:H₂O/TFA-t was applied as eluent [ACN: acetonitrile; TFA: trifluoroacetic acid]. TFA was contained only in water in 0.005 M concentration. Yield: 0.21 g (66%).

¹H NMR [360 MHz, D₂O] δ 7.92 (1H, t, aromatic), 7.40 (4H, m, aromatic) 7.30-7.25 (6H, m, aromatic) 7.31 (2H, d, aromatic) 3.95 (4H, s, CH₂) 3.45-3.22 (8H, m, CH₂) 3.29 (4H, s, CH₂) 2.67 (4H, m, CH₂) 2.59 (4H, d, CH₂) 2.52 (4H, m, CH₂) 2.1 (2H, m, CH) 1.69-1.23 (8H, m, CH₂)

17

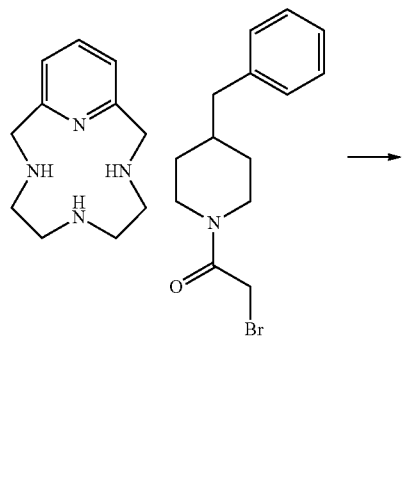

→

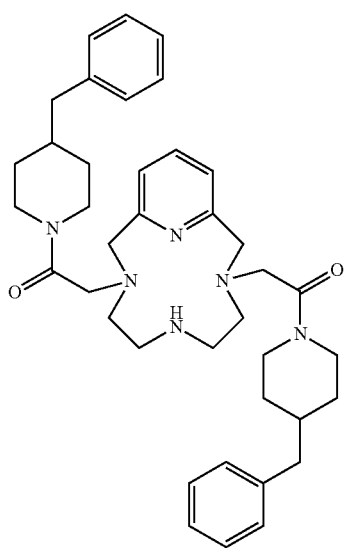

EXAMPLE 10

Synthesis of tPC2AM$^{PypBnNO2}$ a.) N-bromoacetyl-4-(4'-nitrobenzyl)piperidine: Bromoacetyl bromide (3.56 g, 17.6 mmol, 1.55 ml, 1.5 equivalent), dry CH$_2$Cl$_2$ (50 ml) and K$_3$PO$_4$ (6.41 g, 30.2 mmol, 2.5 equ.) was mixed in a flask of 250 ml under N$_2$ atmosphere. 4-(4'-nitrobenzyl)piperidine (2.57 g, 11.7 mmol, 1.0 equivalent) was dissolved in dry CH$_2$Cl$_2$ (20 ml) and was added dropwise to dichloromethane solution of bromoacetyl bromide at 0° C. in 30 minutes, then the reaction mixture was stirred for additional 12 hours at room temperature under N$_2$ atmosphere before the aqueous HCl solution (0.5 M, 30 ml) was added to the reaction mixture. After the addition of HCl solution, the reaction mixture was stirred for additional 5 minutes, then the two phases were separated using a separatory funnel. The aqueous phase was washed with CH$_2$Cl$_2$ (1×15 ml) and then the unified organic phases were washed with KHCO$_3$ solution (2×30 ml, 10 m/m %) and saturated

18

NaCl solution (1×30 ml). The organic phase was dried with MgSO$_4$, then dichloromethane was evaporated at reduced pressure, and the crude product was stored at −20° C. until further use. Yield: 2.43 g (61%).

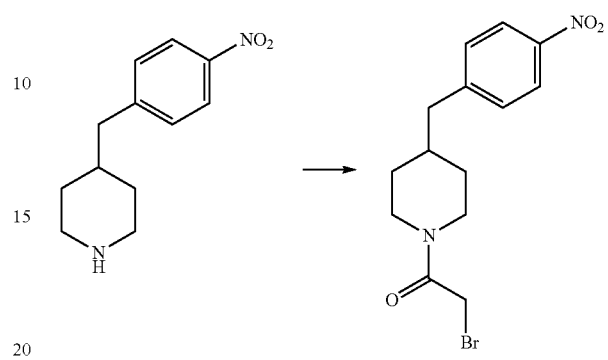

$^1$H NMR [360 MHz, CDCl$_3$] δ 1.90 (1H, m, CH) 1.62-1.33 (8H, m, CH$_2$) 2.56 (2H, m, CH$_2$) 4.21 (2H, s, (CH$_2$), 7.40-8.3 (4H, m, aromatic)

b.) Synthesis of tPC2AM$^{PypBnNO2}$: The N-bromoacetyl-4-(4'-nitrobenzyl)piperidine obtained as described above (0.37 g, 1.08 mmol, 2.2 equivalent) was dissolved in dry acetonitrile and added dropwise to the acetonitrile solution (30 ml) of 3,6,9,15-tetraazabicyclo[9.3.1]pentadeca-1(14),11(15),12-triene (0.10 g, 0.49 mmol, 1 equivalent) and K$_2$CO$_3$ (0.2 g, 1.47 mmol, 3 equivalent) at room temperature within 30 minutes. Then the reaction mixture was refluxed in N$_2$ atmosphere for 24 hours. After 24 hours, K$_2$CO$_3$ was filtered from the hot solution, and acetonitrile was evaporated at reduced pressure. The obtained crude product was purified with HPLC (Luna 10u-Prep C18(2) 100A (250× 21.20 mm; 10 μm) column), ACN:H$_2$O/TFA-t was applied as eluent [ACN: acetonitrile; TFA: trifluoroacetic acid]. TFA was contained only in water in 0.005 M concentration. Yield: 0.25 g (69%).

$^1$H NMR [360 MHz, D$_2$O] δ 8.21 (4H, m, aromatic) 7.93 (1H, t, aromatic), 7.75 (4H, m, aromatic) 7.31 (2H, d, aromatic) 4.11 (4H, s, CH$_2$) 3.50-3.20 (8H, m, CH$_2$) 3.41 (4H, s, CH$_2$) 2.71 (4H, m, CH$_2$) 2.66 (4H, d, CH$_2$) 2.59 (4H, m, CH$_2$) 2.12 (2H, m, CH) 1.70-1.35 (8H, m, CH$_2$)

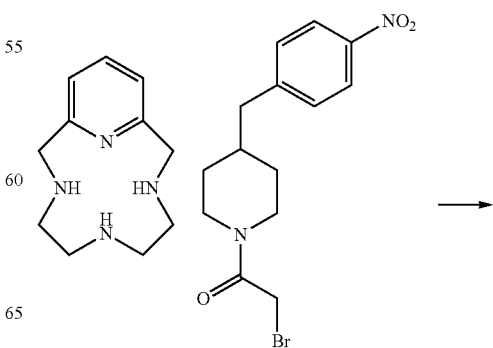

→

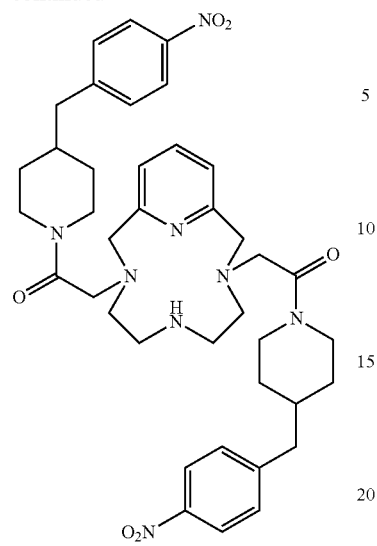

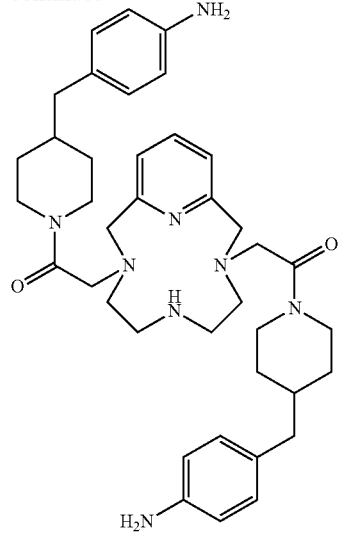

c). Synthesis of tPC2AM$^{PypBnNH2}$: The above obtained tPC2AM$^{PypBnNO2}$ (0.4 g, 0.55 mmol) was dissolved in dry methanol, 0.04 g Pd-carbon catalyst was added, and then the mixture was reduced under 1 bar hydrogen pressure at room temperature for 2 hours. Then filter the catalyst was removed by filtration, the filtrate was evaporated at reduced pressure. Yield: 0.33 g (89%).

$^1$H NMR [360 MHz, D$_2$O] δ 7.92 (1H, t, aromatic), 7.30 (2H, d, aromatic) 7.12 (4H, m, aromatic) 6.44 (4H, m, aromatic) 4.11 (4H, s, CH$_2$) 3.48-3.21 (8H, m, CH$_2$) 3.31 (4H, s, CH$_2$) 2.70 (4H, m, CH$_2$) 2.68 (4H, d, CH$_2$) 2.56 (4H, m, CH$_2$) 1.92 (2H, m, CH) 1.66-1.21 (8H, m, CH$_2$)

d). Synthesis of tPC2AM$^{PypBnNH2}$(0.20 g, 0.30 mmol, 1.0 equivalent) obtained as described above was dissolved in chloroform (50 ml) and cooled to 0° C., then solution of K$_2$CO$_3$ prepared with 30 ml water was added (0.09 g, 0.60 mmol, 2 equivalent) and thiophosgene (0.07 g, 0.60 mmol, equivalent) solution prepared with 30 ml chloroform was also added. Then the mixture was allowed to warm up to room temperature for 5 hours. The organic phase was separated, washed with water (1×10 ml), dried on MgSO$_4$, and then the chloroform was evaporated at reduced pressure. The obtained crude product was purified with HPLC (Luna 10u-Prep C18(2) 100A (250×21.20 mm; 10 μm) column), ACN:H$_2$O/TFA-t was applied as eluent [ACN: acetonitrile; TFA: trifluoroacetic acid]. TFA was contained only in water in 0.005 M concentration. Yield: 0.13 g (56%). $^1$H NMR [360 MHz, D$_2$O] δ 7.91 (1H, t, aromatic), 7.28 (2H, d, aromatic) 7.40-7.18 (8H, m, aromatic) 3.95 (4H, s, CH$_2$) 3.39-3.29 (8H, m, piperidine CH$_2$) 3.33 (4H, s, CH$_2$) 2.65 (4H, m, CH$_2$) 2.54 (4H, d, CH$_2$) 2.51 (4H, m, CH$_2$) 1.98 (2H, m, CH) 1.65-1.33 (8H, m, CH$_2$)

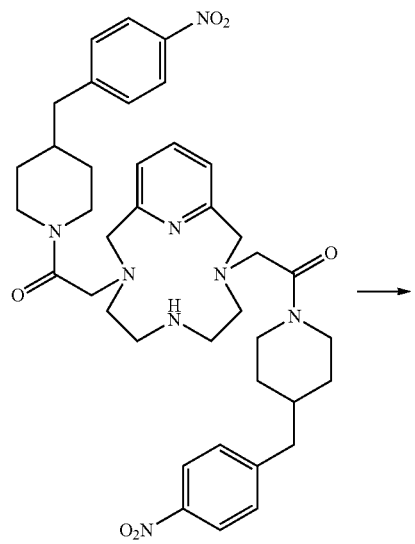

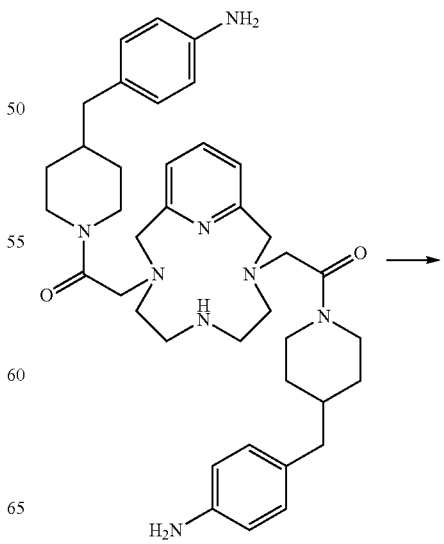

-continued

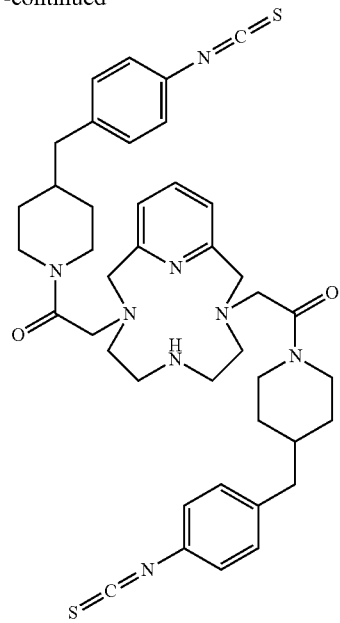

-continued

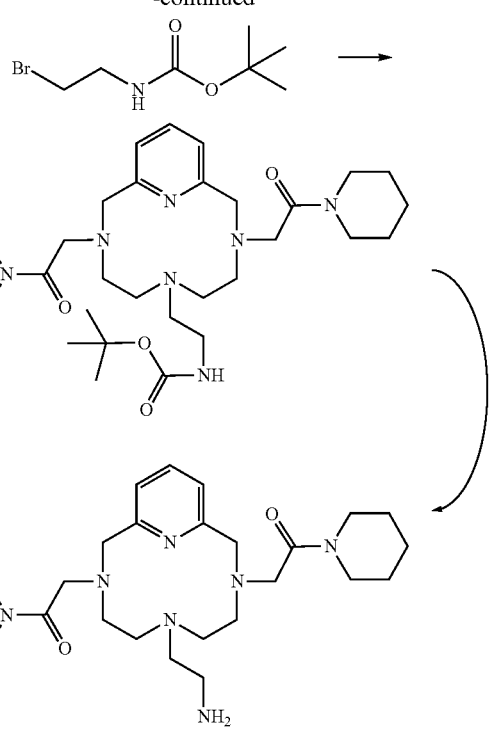

EXAMPLE 11

Synthesis of tPC2AMP$^{Pyp}$EA

The tert-butyl N-(2-bromoethyl)carbamate (0.09 g, 0.40 mmol, 1.3 equivalent) was dissolved in dry acetonitrile, and then added dropwise at room temperature to the acetonitrile solution (30 ml) of the tPC2AMP$^{Pyp}$ ligand manufactured as per Example 1 (0.14 g, 0.31 mmol, 1 equivalent) (prepared on the basis of *Organic Preparations and Procedures International,* 2009, 41(4), 301-307 publication by Li, Hongbo; Hao, Meng-an; Wang, Liping; Liang, Wu; Chen, Kai From) and K$_2$CO$_3$ (0.09 g, 0.62 mmol, 2 equivalent) within 30 minutes. Then the reaction mixture was refluxed in N$_2$ atmosphere for 24 hours. After 24 hours, K$_2$CO$_3$ was filtered from the hot solution, and the filtrate was evaporated at reduced pressure. The obtained crude product was purified with HPLC (Luna 10u-Prep C18(2) 100A (250×21.20 mm; 10 μm) column), ACN:H$_2$O/TFA-t was applied as eluent [ACN: acetonitrile; TFA: trifluoroacetic acid]. TFA was contained only in water in 0.005 M concentration. The oily material obtained after purification (10 ml) was dissolved in CH2Cl2, then trifluoroacetic acid was added to it (0.07 ml, 3 equivalent) and the reaction mixture was refluxed for 24 hours. Then the solvent was evaporated at reduced pressure, once 6 M (10 ml), and twice water (10-10 ml) was evaporated from the solid to remove trifluoroacetic acid excess. Yield: 0.09 g (58%).

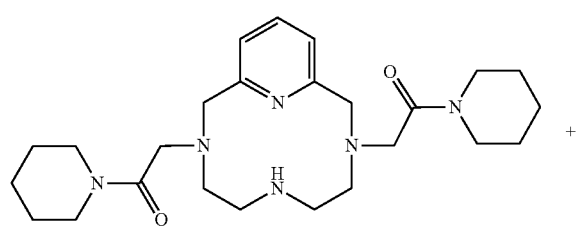
+

$^1$H NMR [360 MHz, D$_2$O] δ 1.4-1.7 (12H, m, (6pcs CH$_2$)), 2.68 (4H, d, 2pcs CH$_2$), 3.32 (8H, m, (4pcs CH$_2$)), 3.4-3.6 (8H, m, (4pcs CH$_2$)), 4.32 (4H, s, (2pcs CH$_2$)), 4.62 (4H, s, (2pcs CH$_2$)), 7.63 (2H, d, (CH) aromatic), 8.16 (1H, t, (CH) aromatic);

$^{13}$C NMR [100 MHz, D$_2$O] δ 23.2 2pcs CH$_2$; 25.1 2pcs CH$_2$; 25.4 2pcs CH$_2$; 40.2 1pc CH$_2$; 43.5 2pcs CH$_2$; 44.3 2pcs CH$_2$; 45.7 2pcs CH$_2$; 53.0 2pcs CH$_2$; 55.1 1pc CH$_2$; 57.5 2pcs CH$_2$; 58.3 2pcs CH$_2$; 123.1 2pcs CH aromatic; 143.2 CH aromatic; 153.1 2pcs C aromatic; 169.6 2pcs C(=O);

EXAMPLE 12

Synthesis of tPC2AMP$^{Pyp}$DPA

The 2-(chloromethyl)pyridine (0.088 g, 0.69 mmol, 2.3 equivalent) was converted into the commercially available 2-(chloromethyl)pyridine hydrochloride free base form was dissolved in dry acetonitrile and was added dropwise to the acetonitrile solution (30 ml) of the tPC2AMPPypEA ligand (0.15 g, 0.30 mmol, 1 equivalent) and N,N-diisopropylethylamine (0.12 g, 0.90 mmol, 3 equivalent) at room temperature within 30 minutes. Then the reaction mixture was refluxed in N$_2$ atmosphere for 24 hours and was evaporated at reduced pressure. The obtained crude product was purified with HPLC (Luna 10u-Prep C18(2) 100A (250×21.20 mm; 10 μm) column), ACN:H$_2$O/TFA-t was applied as eluent [ACN: acetonitrile; TFA: trifluoroacetic acid]. TFA was contained only in water in 0.005 M concentration. Yield: 0.12 g (60%).

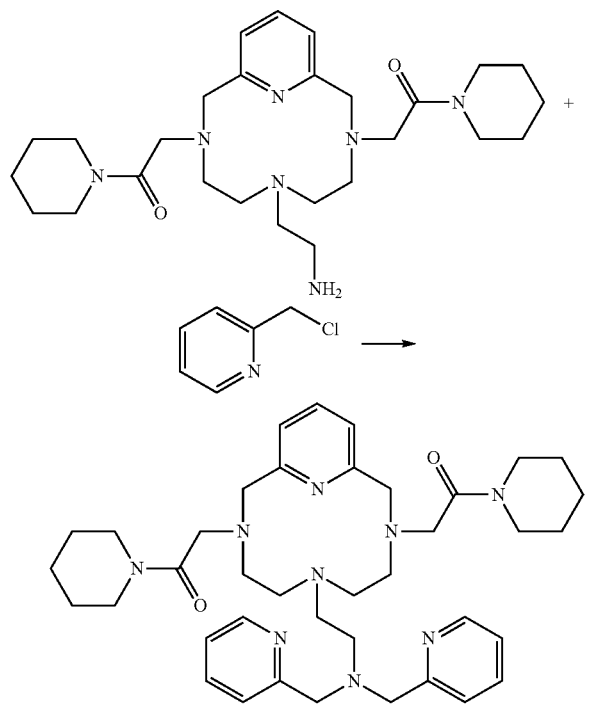

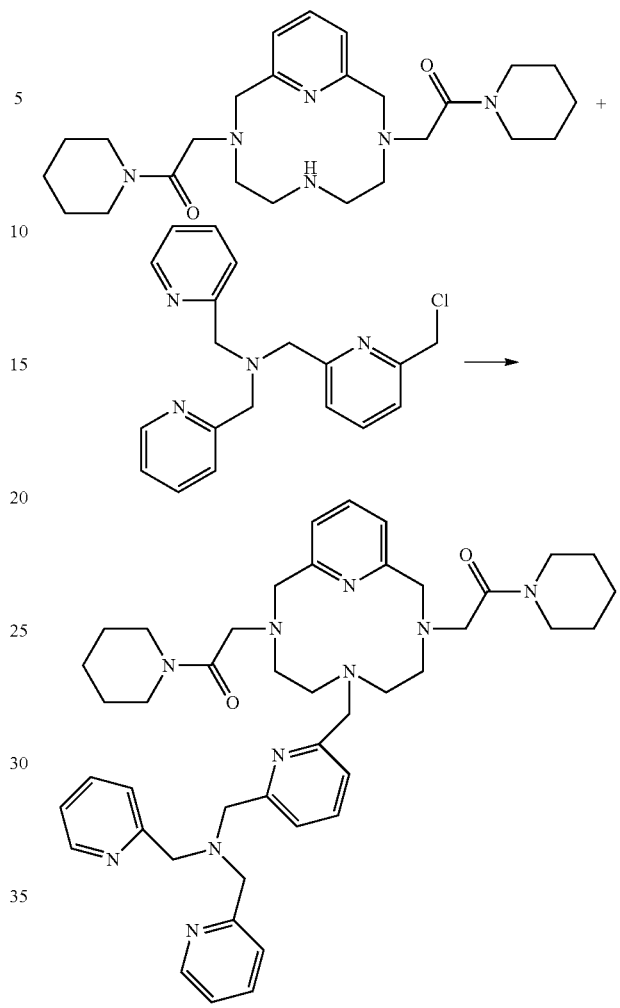

¹H NMR [360 MHz, D₂O] δ 1.4-1.7 (12H, m, (6pcs CH₂)), 2.51 (4H, d, 2pcs CH₂) 3.32 (8H, m, (4pcs CH₂)), 3.4-3.6 (8H, m, (4pcs CH₂)), 4.11 (4H, s, (2pcs CH₂)), 4.32 (4H, s, (2pcs CH₂)), 4.62 (4H, s, (2pcs CH₂)), 7.26 (4H, t, (CH) aromatic), 7.64 (2H, d, (CH) aromatic), 7.72 (2H, t, (CH) aromatic), 8.16 (1H, t, (CH) aromatic), 8.29 (2H, d, (CH) aromatic), ¹³C NMR [100 MHz, D₂O] δ 24.8 2pcs CH₂; 25.3 2pcs CH₂; 25.8 2pcs CH₂; 41.0 1pc CH₂; 44.4 2pcs CH₂; 44.9 2pcs CH₂; 45.9 2pcs CH₂; 53.3 2pcs CH₂; 56.3 1pc CH₂; 58.3 2pcs CH₂; 58.9 2pcs CH₂; 119.1 2pcs CH aromatic; 123.1 2pcs CH aromatic; 126.0 2pcs CH aromatic; 141.1 2pcs CH aromatic; 143.2 CH aromatic; 149.1 2pcs CH aromatic; 153.1 2pcs C aromatic; 158.1 2pcs CH aromatic; 169.6 2pcs C(=O);

EXAMPLE 13

Synthesis of tPC2AMP$^{Pyp}$TPA

The 1-(6-(chloromethyl)pyridine-2-yl)-N,N-bis(pyridine-2-ylmethyl)methaneamine (0.15 g, 0.43 mmol, 1.3 equivalent, manufactured on the basis of *Dalton Trans.*, 2006, 3108-3113 publication by Simon J. A. Pope, Rebecca H. Laye) was dissolved in dry acetonitrile, and then added dropwise at room temperature to the acetonitrile solution (30 ml) of the tPC2AMP tPC2AM$^{Pyp}$ ligand (0.15 g, 0.30 mmol, 1 equivalent) and K₂CO₃ (0.12 g, 0.90 mmol, 3 equivalent) within 30 minutes. Then the reaction mixture was refluxed in N₂ atmosphere for 24 hours. After 24 hours, K₂CO₃ was filtered from the hot solution, and the reaction mixture was evaporated at reduced pressure. The obtained crude product was purified with HPLC (Luna 10u-Prep C18(2) 100A (250×21.20 mm; 10 µm) column), ACN:H2O/TFA-t was applied as eluent [ACN: acetonitrile; TFA: trifluoroacetic acid]. TFA was contained only in water in 0.005 M concentration. Yield: 0.15 g (65%).

¹H NMR [360 MHz, D₂O] δ 1.4-1.7 (12H, m, (6pcs CH₂)), 2.68 (4H, d, 2pcs CH₂) 3.32 (8H, m, (4pcs CH₂)), 3.4-3.6 (8H, m, (4pcs CH₂)), 4.14 (8H, s, 4pcs CH₂) 4.62 (4H, s, (2pcs CH₂)), 7.63 (2H, d, (CH) aromatic), 7.71 (2H, d, (CH) aromatic), 7.88 (4H, m, (CH) aromatic), 8.16 (1H, t, (CH) aromatic), 8.32 (3H, t, (CH) aromatic);

¹³C NMR [100 MHz, D₂O] δ 23.2 2pcs CH₂; 25.1 2pcs CH₂; 25.4 2pcs CH₂; 40.2 1pc CH₂; 43.5 2pcs CH₂; 44.3 2pcs CH₂; 53.0 2pcs CH₂; 55.1 1pc CH₂; 57.5 2pcs CH₂; 58.3 2pcs CH₂; 62.1 3pcs CH₂; 63.9 1pc CH₂; 123.1 2pcs CH aromatic; 122.7 4pcs CH aromatic; 124.9 2pcs CH aromatic; 143.2 2pcs CH aromatic; 146.4 2pcs CH aromatic; 149.0 2pcs CH aromatic; 153.1 2pcs C aromatic; 154.1 2pcs C aromatic; 158.4 2pcs C aromatic; 173.3 2pcs C(=O);

EXAMPLE 14

Synthesis of pOH-tPC2A

The commercially available tert-butyl bromoacetate (0.19 g, 0.99 mmol, 0.145 ml, 2.2 equivalent) was dissolved in dry acetonitrile, then added dropwise to the acetonitrile solution (30 ml) of 3,6,9,15-tetraazabicyclo[9.3.1]pentadeca-1(14),11(15),12-triene-13-ol (0.10 g, 0.45 mmol, 1 equivalent) and K₂CO₃ (0.19 g, 1.35 mmol, 3 equivalent) at room temperature within 30 minutes (the macrocycle was manufactured based on the K. M. Lincoln, M. E. Offutt, T, D. Hayden, R. E. Saunders, K. N. Green, *Inorg, Chem.*, 2014, 53(3), 1406-1416, and K. M. Lincoln, P. Gonzalz, T. E: Richardson, D. A. Julovich, R. Saunders, J. W. Simpkins, K. N. Green, *Chem. Commun.*, 2013, 49(26), 2712-2714 publications). Then the reaction mixture was refluxed in $N_2$ atmosphere for 24 hours. After 24 hours, $K_2CO_3$ was filtered from the hot solution, and acetonitrile was evaporated at reduced pressure. The obtained crude product was purified with HPLC (Luna 10u-Prep C18(2) 100A (250×21.20 mm; 10 μm) column), ACN:$H_2O$/TFA-t was applied as eluent [ACN: acetonitrile; TFA: trifluoroacetic acid]. TFA was contained only in water in 0.005 M concentration. The obtained yellowish oil was dissolved in 10 ml $CH_2Cl_2$, then trifluoroacetic acid was added to it (0.21 ml, 6 equivalent) and the reaction mixture was refluxed for 24 hours. Then the solvent was evaporated at reduced pressure, once 6 M (10 ml), and twice water (10-10 ml) was evaporated from the solid to remove trifluoroacetic acid excess. Yield: 0.11 g (72%).

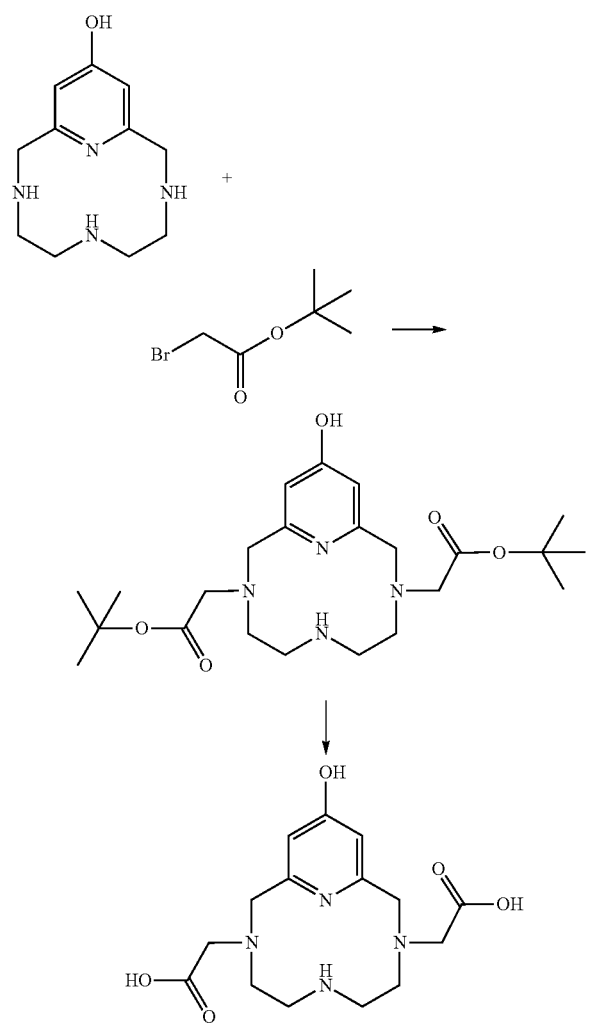

$^1$H NMR [360 MHz, $D_2O$] δ 3.23 (2H, m, ($CH_2$)), 3.3-3.5 (8H, m, (4pcs $CH_2$)), 3.43 (4H, s, (2pcs $CH_2$)), 3.81 (2H, m, ($CH_2$)), 6.40 (2H, s, (CH) aromatic);

$^{13}$C NMR [100 MHz, $D_2O$] δ 46.2 2pcs $CH_2$; 57.5 2pcs $CH_2$; 60.0 2pcs $CH_2$; 64.3 2pcs $CH_2$; 113.3 2pcs CH aromatic; 153.0 C(OH) aromatic; 158.2 2pcs C aromatic; 161.6 2pcs C(=O);

EXAMPLE 15

Synthesis of pOH-tPC2AM$^{Pyp}$

The 2-bromo-1-(piperidine-1-yl)ethanone manufactured as per Example 1 (0.21 g, 0.99 mmol, 2.2 equivalent) was dissolved in dry acetonitrile, then added dropwise to the acetonitrile solution (30 ml) of 3,6,9,15-tetraazabicyclo [9.3.1]pentadeca-1(14),11(15),12-triene-13-ol (0.10 g, 0.45 mmol, 1 equivalent) and $K_2CO_3$ (0.19 g, 1.35 mmol, 3 equivalent) at room temperature within 30 minutes (the macrocycle was manufactured based on the K. M. Lincoln, M. E. Offutt, T. D. Hayden, R. E. Saunders, K. N. Green, *Inorg, Chem.*, 2014, 53(3), 1406-1416, and K. M. Lincoln, P. Gonzalz, T. E: Richardson, D. A. Julovich, R. Saunders, J. W. Simpkins, K. N. Green, *Chem. Commun.*, 2013, 49(26), 2712-2714 publications). Then the reaction mixture was refluxed in $N_2$ atmosphere for 24 hours. After 24 hours, $K_2CO_3$ was filtered from the hot solution, and the mother liquor was evaporated at reduced pressure. The obtained crude product was purified with HPLC (Luna 10u-Prep C18(2) 100A (250×21.20 mm; 10 μm) column), ACN:$H_2O$/ TFA-t was applied as eluent [ACM acetonitrile; TFA: trifluoroacetic acid]. TFA was contained only in water in 0.005 M concentration. Then the solvent was evaporated at reduced pressure, once 6 M (10 ml) hydrochloric acid, and twice water (10-10 ml) was evaporated from the solid to remove trifluoroacetic acid excess. Yield: 0.11 g (57%).

$^1$H NMR [360 MHz, $D_2O$] δ 1.52 (12H, m, (6pcs $CH_2$)), 2.84 (4H, m, (2pcs $CH_2$)), 3.23 (2H, m, ($CH_2$)), 3.3-3.6 (8H, m, (4pcs $CH_2$)), 3.87 (2H, m, ($CH_2$)), 4.84 (4H, s, (2pcs $CH_2$), 6.38 (2H, s, (CH) aromatic);

$^{13}$C NMR [100 MHz, $D_2O$] δ 24.3 2pcs $CH_2$; 24.7 2pcs $CH_2$; 25.8 2pcs $CH_2$; 43.9 4pcs $CH_2$; 45.1 2pcs $CH_2$; 46.4 2pcs $CH_2$; 58.0 2pcs $CH_2$; 60.3 2pcs $CH_2$; 114.0 2pcs CH aromatic; 157.0 C(OH) aromatic; 159.4 2pcs C aromatic; 159.0 2pcs C(=O);

EXAMPLE 16

Synthesis of tPC2AM$^{OMe}$

The commercially available tert-butyl bromoacetate (0.27 g, 1.40 mmol, 0.20 ml, 2.2 equivalent) was dissolved in dry acetonitrile, then added dropwise to the acetonitrile solution (30 ml) of 3,6,9,15-tetraazabicyclo[9.3.1]pentadeca-1(14),11(15),12-triene-13-methoxy (0.15 g, 0.63 mmol, 1 equivalent) and K$_2$CO$_3$ (0.26 g, 1.89 mmol, 3 equivalent) at room temperature within 30 minutes (the macrocycle was manufactured based on the K. M. Lincoln, M. E. Offutt, T. D. Hayden, R. E. Saunders, K. N. Green, *Inorg. Chem.*, 2014, 53(3), 1406-1416, and K. M. Lincoln, P. Gonzalz, T. E: Richardson, D. A. Julovich, R. Saunders, J. W. Simpkins, K. N. Green, *Chem. Commun.*, 2013, 49(26), 2712-2714 publications). Then the reaction mixture was refluxed in N$_2$ atmosphere for 24 hours. After 24 hours, K$_2$CO$_3$ was filtered from the hot solution, and the filtrate was evaporated at reduced pressure. The obtained crude product was purified with HPLC (Luna 10u-Prep C18(2) 100A (250×21.20 mm; 10 μm) column), ACN:H$_2$O/TFA-t was applied as eluent [ACN: acetonitrile; TFA: trifluoroacetic acid]. TFA was contained only in water in 0.005 M concentration. The obtained yellowish oil was dissolved in CH$_2$Cl$_2$ (10 ml), then trifluoroacetic acid is added to it (0.24 ml, 6 equivalent) and the reaction mixture was refluxed for 24 hours. Then the solvent was evaporated at reduced pressure, once 6 M (10 ml), and twice water (10-10 ml) was evaporated from the solid to remove trifluoroacetic acid excess. Yield: 0.13 g (59%).

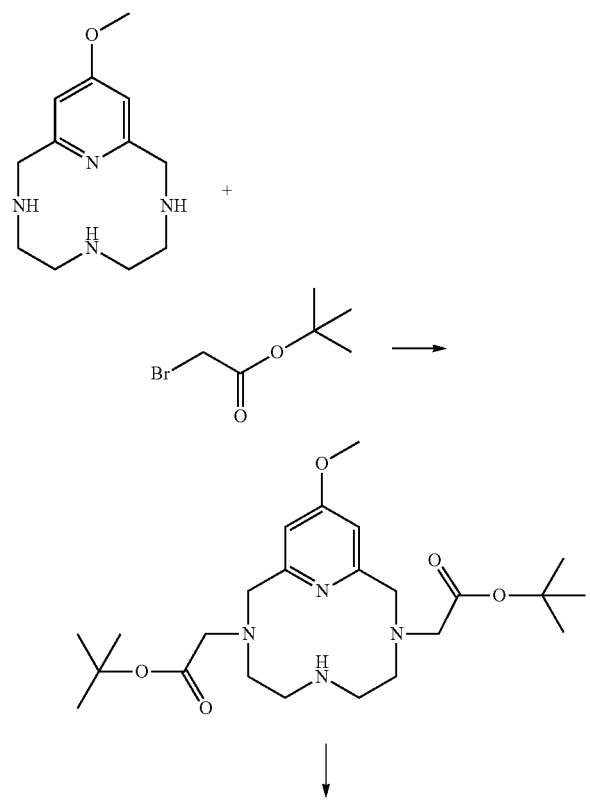

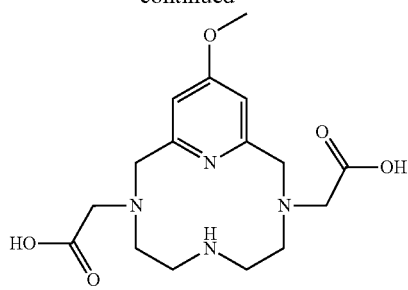

$^1$H NMR [360 MHz, D$_2$O] δ 3.21 (2H, m, (CH$_2$)), 3.24-3.47 (8H, m, (4pcs CH$_2$)), 3.41 (4H, s, (2pcs CH$_2$), 3.78 (2H, m, (CH$_2$)), 3.81 (3H, s, CH$_3$), 6.42 (2H, s, (CH) aromatic);

$^{13}$C NMR [100 MHz, D$_2$O] δ 47.1 2pcs CH$_2$; 56.2 1pc CH$_3$ 57.8 2 pcs CH$_2$; 61.1 2pcs CH$_2$; 63.9 2pcs CH$_2$; 112.1 2pcs CH aromatic; 157.9 2pcs C aromatic; 161.1 C(OCH$_3$) aromatic; 169.7 2pcs C(=O);

EXAMPLE 17

Synthesis of tPC2AMP$^{Pyp}$OMe

The 2-bromo-1-(pyperidine-1-yl)ethanone manufactured as per Example 1 (0.29 g, 1.40 mmol, 2.2 equivalent) was dissolved in dry acetonitrile, then added dropwise to the acetonitrile solution (30 ml) of 3,6,9,15-tetraazabicyclo[9.3.1]pentadeca-1(14),11(15),12-triene-13-methoxy (0.15 g, 0.63 mmol, 1 equivalent) and K$_2$CO$_3$ (0.26 g, 1.89 mmol, 3 equivalent) at room temperature within 30 minutes (the macrocycle was manufactured based on the K. M. Lincoln, M. E. Offutt, T. D. Hayden, R. E. Saunders, K. N. Green, *Inorg. Chem.*, 2014, 53(3), 1406-1416, and K. M. Lincoln, P. Gonzalez, T. E: Richardson, D. A. Julovich, R. Saunders, J. W. Simpkins, K. N. Green, *Chem. Commun.*, 2013, 49(26), 2712-2714 publications). Then the reaction mixture was refluxed in N$_2$ atmosphere for 24 hours. After 24 hours, K$_2$CO$_3$ was filtered from the hot solution, and the filtrate was evaporated at reduced pressure. The obtained crude product was purified with HPLC (Luna 10u-Prep C18(2) 100A (250×21.20 mm; 10 μm) column), ACN:H$_2$O/TFA-t was applied as eluent [ACN: acetonitrile; TFA: trifluoroacetic acid]. TFA was contained only in water in 0.005 M concentration. The fraction containing the product was evaporated at reduced pressure, once 6 M hydrochloric acid (10 ml), and twice water (10-10 ml) was evaporated from the solid to remove trifluoroacetic acid excess. Yield: 0.14 g (46%).

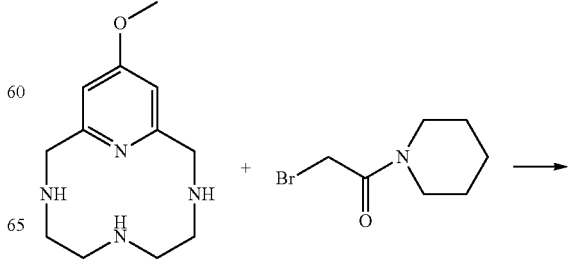

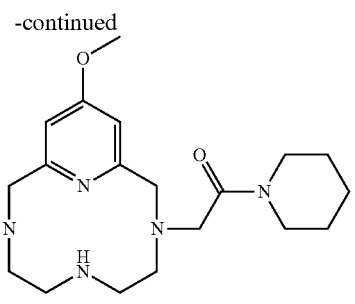

$^1$H NMR [360 MHz, D$_2$O] δ 1.52 (12H, m, (6pcs CH$_2$)), 2.84 (4H, m, (2pcs CH$_2$)), 3.23 (2H, m, (CH$_2$)), 3.3-3.6 (8H, m, (4pcs CH$_2$)), 3.87 (2H, m, (CH$_2$)), 4.84 (4H, s, (2pcs CH$_2$), 6.38 (2H, s, (CH) aromatic);

$^{13}$C NMR [100 MHz, D$_2$O] δ 24.5 2pcs CH$_2$; 24.8 2pcs CH$_2$; 25.9 2pcs CH$_2$; 44.2 4pcs CH$_2$; 45.5 2pcs CH$_2$; 46.0 2pcs CH$_2$; 57.2 1pc CH$_3$, 57.6 2pcs CH$_2$; 60.1 2pcs CH$_2$; 112.8 2pcs CH aromatic; 155.5 C(OCH$_3$) aromatic; 161.4 2pcs C aromatic; 170.1 2pcs C(=O);

EXAMPLE 18

Efficacy Data

During the physico-chemical tests of tPC2AM$^{Pyp}$ and tPC2AM$^{Pro}$ compounds synthesized according to Example 1 and 2, their protonation constant, as well as equilibrium behaviour and kinetic inertism of their Mn(II) complexes was studied in detail, and the characteristic relaxivity values of the complexes were determined in the presence and absence of HSA (Human Serum Albumin), at 25 and 37° C. and physiological pH. All studies were performed in the presence of 0.15 M NaCl, the same concentration as that of the electrolyte under physiological conditions.

The results of equilibrium study are summarized in Table 1, in addition to the protonation constants, total basicity of ligands and stability constants of their Mn(II) complexes, the pMn value calculated for complexes are also represented in the table.

TABLE 1

Protonation constants and total basicity of the studied ligands, stability constants of their Mn(II) complexes and calculated pMn values (25° C., 0.15 M NaCl).

| | logK$_1$ | logK$_2$ | logK$_3$ | logK$_4$ | ΣlogK$_i^H$ | logK$_{MnL}$ | pMn |
|---|---|---|---|---|---|---|---|
| tPC2AM$^{Pyp}$ | 11.31(1) | 3.94(3) | — | — | 15.26 | 13.09(2) | 7.09 |
| tPC2AM$^{Pro}$ | 9.80(2) | 7.96(4) | 3.65(5) | 2.26(4) | 23.67 | 13.77(3) | 7.85 | pMn values were calculated by using the equilibrium constants at pH = 7.4 and cMn = cL = 10$^{-5}$ M.

Based on the pMn values represented in Table 1 (calculated using the equilibrium constants at pH=7.4 and cMn=cL=10$^{-5}$ M), it can be concluded that the studied Mn(II) complexes are formed in 100% at physiological pH, which is an essential aspect of the practical use.

An important parameter of using Mn(II) containing contrast agents in vivo is the low kinetic reactivity of the complex. The kinetic reactivity is generally tested with metal ion exchange reactions, where the replacing metal ion is Zn(II) or Cu(II) in most of the cases. The application of Cu(II) is advantageous for more reasons, in one hand the complexes with ligands are of great thermodynamic stability, so relatively small excess of Cu(II) ion leads to complete replacement, on the other hand molar absorbance values of Cu(II) complexes both in UV and visible range are sufficiently high to enable spectrophotometric method for examinations even at low concentrations. Moreover, the endogenic characteristic of the Cu(II) ion provides additional information on in vivo processes. Replacement reactions were executed with at least 10-fold excess Cu(II) ion concentration to ensure pseudo-primary conditions.

Dissociation reactions of Mn(II) complexes may take place in several pathways as represented below.

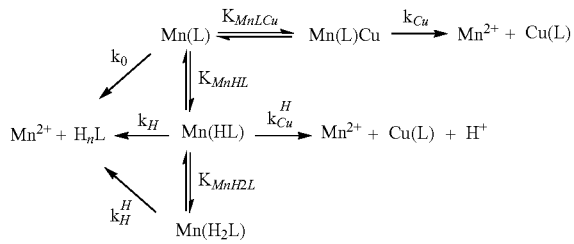

The $k_0$, $k_H$, $k_H^H$, $k_{Cu}$ and $k_{Cu}^H$, rate constants indicate the spontaneous, proton associated, metal assisted and proton-metal assisted (when the replacing metal ion attacks the protonated complex) reaction pathways of the complex. The $K_{MnHL}$, $K_{MnH_2L}$ and $K_{MnLCu}$ are stability constants of the protonated and binuclear intermediate complexes.

In case of metal complexes formed with macrocyclic ligands the above detailed mechanism involves only proton associated dissociation pathways (in some instances spontaneous dissociation may have some role), since the formation of binuclear complexes are inhibited (denticity of rigid ligands does not exceed the coordination number of the metal ion, Mn$^{2+}$). Due to this reason, replacement reactions were executed in 2.0-5.0 pH range with only 10-fold Cu(II) replacement metal ion excess.

In general the $k_{obs}$ pseudo-primary rate constants obtained in each reaction are given with the following equation, where the stability constants of each reaction pathway and that of the forming intermediate are also considered:

$$k_{obs} = \frac{k_0 + k_1[H^+] + k_2[H^+]^2 + k_3[Cu^{2+}] + k_4[Cu^{2+}][H^+]}{1 + K_{MnHL}[H^+] + K_{MnH_2L}[H^+]^2 + K_{MnLCu}[Cu^{2+}]}, \quad (1)$$

whereas $K_{MnHL}$=[Mn(HL)]/[Mn(L)][H$^+$], $K_{MnH_2L}$=[Mn(H$_2$L)]/[Mn(HL)][H$^+$], $K_{MnLCu}$=[Mn(L)M]/[Mn(L)][M], $k_1$=$k_H \cdot K_{MnHL}$, $k_2$=$k_H^H \cdot K_{MnHL} \cdot K_{MnH_2L}$, $k_3$=$k_{Cu} \cdot K_{MnLCu}$ $k_4$=$k_{Cu}^H \cdot K_{MnHL}$ Results of the kinetic study showed that in the dissociation of [Mn(tPC2AM$^{Pyp}$)]$^{2+}$ complexes, the proton associated dissociation, characterized with $k_1$ plays an important role. Using these rate constants the half-life (t$_{1/2}$) of [Mn $(tPC2AM^{Pyp})]^{2+}$ and $[Mn(tPC2AM^{Pro})]^{2+}$ complex dissociation may be calculated at physiologic pH, being 352 and 215 hours.

In order to estimate the quantity of complex decomposing in the body, it is useful to handle elimination and complex dissociation as parallel, primary reaction characterized by the (2) equation set for $Gd^{3+}$ complexes [F. K. Kálmán and G. Tircsó, Inorg. Chem., 2012, 51, 10065]:

$$[GdL]_d = \frac{k_d}{k_d + k_{ex}}[GdL]_0(1 - e^{-(k_d+k_{ex})t}) \quad (2)$$

The equation indicates that the extent of the dissociation of the complex depends on the ratio of rate constants. For the (renal) elimination of contrast agent 1.6 hour half life can be given in general, characterized by a $k_{ex}=0.433\ 11^{-1}$ rate constant. Using the $k_d$ values of Mn(II) complexes and the $k_{ex}$ values characteristic for elimination, one can calculate the percentile ratio of injected complex dissociated in vivo until complete elimination (12-24 hours). Calculation verified, that less than 0.8% of the complexes would dissociate before the elimination of the complex. Considering the essential character of Mn(II) ion and its complexes the given amount cannot cause significant burden for MRI tested patients. Considering these new results, during the in vivo dissociation (37° C.) of $[Gd(DTPA)]^{2-}$ complex (Magnevist) applied in practice, 2.2% Gd(III) ion releases being 4.4-fold of the value calculated on the basis of experiments at 25° C. (0.5%). [Sarka L. et al, Chem. Eur. J., 2000, 6, 719]. Using this finding, the quantity of in vivo releasing Mn(II) for the presented Mn(II) complexes is approximately 3%. This value is better than some of those applied for Gd containing contrast agents in practice [Baranyai Z et al, Chem. Eur. J., 2015, 21, 4789]

In addition to appropriately low kinetic reactivity, complexes shall also have suitable relaxivity for the purpose of practical use (relaxivity ($mM^{-1}\ s^{-1}$): relaxation rate increase of 1 mM solution of the paramagnetic substance compared to the measured value under diamagnetic conditions [Tóth É., et. al., The Chemistry of Contrast Agents in Medical Magnetic Resonance Imaging, Chichester: John Wiley & Sons, 2001.]). Higher complex relaxivity results in higher contrast increasing effect, meaning that the same image quality is obtained by introducing less amount of complex with higher relaxivity. The relaxivity value of both complexes were determined at pH=7.4 and 25 and 37° C. in the presence and absence of HSA (Human Serum Albumin, c=0.7 mM) to better stimulate conditions of the in vivo application. Relaxivity values of the complexes are presented in Table 2. Comparing the data in Table 2 with the relaxivity values of DOTAREM ($[Gd(DOTA)]^-$ complex, $r_1=3.83\ mM^{-1}\ s^{-1}$) and MAGNEVIST ($[Gd(DTPA)]^{2-}$ complex, $r_1=4.02\ mM^{-1}\ s^{-1}$) [Powell, D. H., Ni Dhubhghaill, O. M., Pubanz, D. et al. (1996) J. Am. Chem. Soc., 118, 9333-9346] applied in practice under the same conditions, the Mn(II) complexes presented herein obviously have higher relaxivities and thus higher contrast increasing effect.

TABLE 2

Relaxivity values of the tested complexes (pH = 7.4)

| Complex | T (° C.) | $r_1$ ($mM^{-1}s^{-1}$) | $r_1$ ($mM^{-1}s^{-1}$) HSA |
|---|---|---|---|
| $[Mn(tPC2AM^{Pyp})]^{2+}$ | 25 | 4.90 | 18.34 |
|  | 37 | 3.96 | 14.07 |
| $[Mn(tPC2AM^{Pro})]$ | 25 | 4.43 | 5.53 |
|  | 37 | 3.44 | 4.36 |

The invention claimed is:

1. A compound of general formula (I)

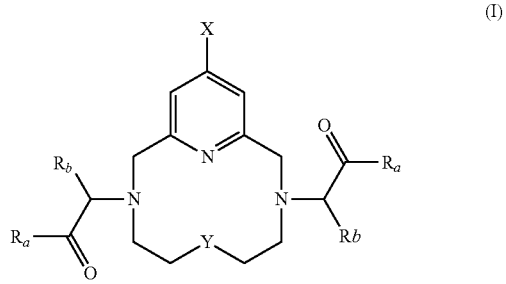

wherein $R_a$ is a —Q group selected from:

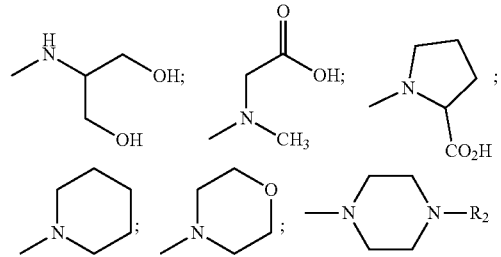

where $R_2$ is a H atom, carboxyl or alkyl-carbonyl;

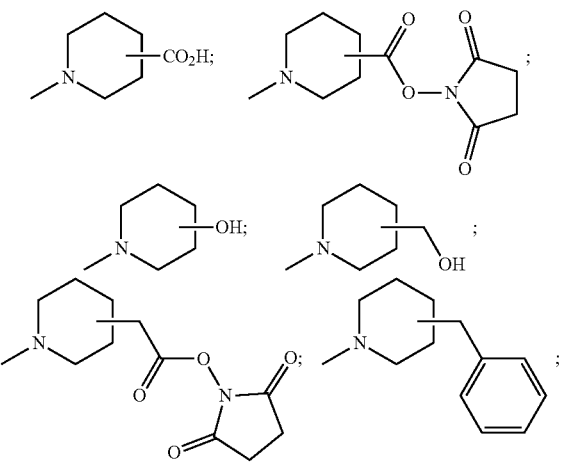

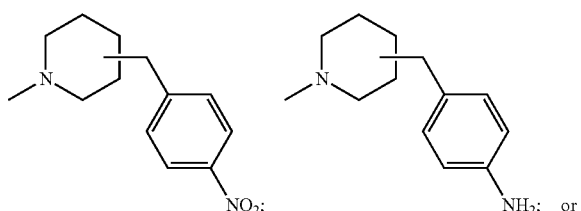

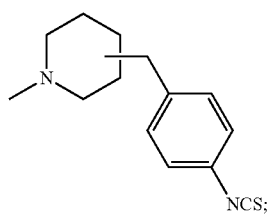

$R_b$ is H-atom or alkyl group;

X is H-atom; and

Y means —NH—, >N—C(O)-Q group where Q is defined as above, or >NCH2-Z group where Z selected from:

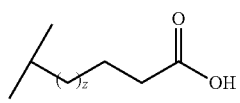

where z=0-18,

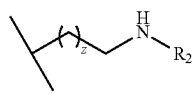

where z=0-18 and $R_2$ is H atom, alkyl, or —(CH$_2$)$_n$—COOH group, where n=1-10,

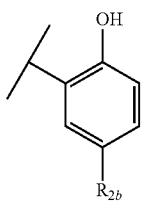

where $R_{2b}$ is H atom, —CH$_3$, —OCH$_3$, —CF$_3$, —COOH, —COON(CO)$_2$(CH$_2$)$_2$, —NO$_2$, —NH$_2$, or —NCS— group,

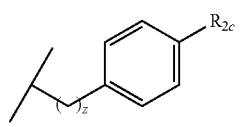

where z=0-18 and $R_{2c}$ is H atom, —NO$_2$, —NH$_2$, or —NCS— group,

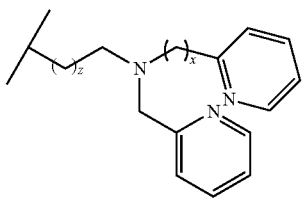

where z=0-18, and x=1-5,

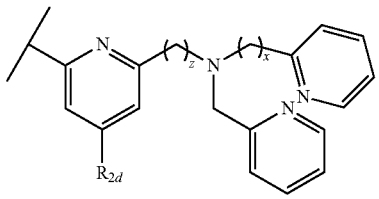

where z=1-5, and x=1-5, $R_{2d}$ is H atom, —CH$_3$, —OCH$_3$, —CF$_3$, —NO$_2$, —NH$_2$, —NCS —COOH, or —COON(CO)$_2$ (CH$_2$)$_2$ group.

2. The compound according to claim 1, wherein the compound is 3,9-bis[2-oxo-2-(piperidine-1-yl)ethyl]-3,6,9,15-tetraazabicyclo[9.3.1]pentadeca-1(15),11,13-triene.

3. A complex comprising the compound of claim 1 and a metal selected from Mn(II), Fe(II), Fe(III), Co(II), or Ni(II).

4. A complex comprising the compound of claim 2 and a metal selected from Mn(II), Fe(II), Fe(III), Co(II), or Ni(II).

5. A method of imaging, comprising:
applying a compound according to claim 1 as a contrast agent in diagnostic imaging, and
performing diagnostic imaging.

6. A method of imaging, comprising:
applying a compound according to claim 2 as a contrast agent in diagnostic imaging, and
performing diagnostic imaging.

7. A contrast agent kit comprising: a compound according to claim 1.

8. A contrast agent kit comprising: a compound according to claim 2.

9. A method of imaging, comprising:
applying a complex according to claim 3 as a contrast agent in diagnostic imaging, and
performing diagnostic imaging.

10. A contrast agent kit comprising: a complex according to claim 3.

11. A compound of general formula (I)

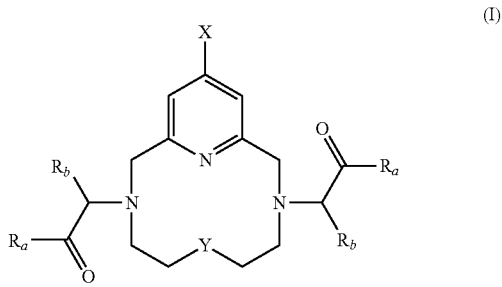

wherein

R$_a$ is —OH group;

R$_b$ is H-atom or alkyl group;

X is —CH$_3$, —COOH, —OH, —OCH$_3$, alkoxy-, —NO$_2$, —NH$_2$, —NCS, —NHS-activated ester, alkyl, or aryl, wherein alkyl and aryl may be optionally substituted with hydroxyl, hydroxyalkyl, nitro, amino, or isothiocyanate group; and Y means —NH—, >N—C(O)-Q group, or >NCH$_2$—Z group, where Q group is selected from:

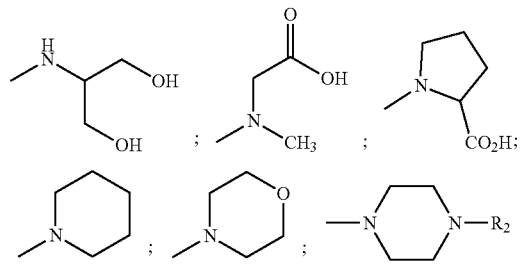

where R$_2$ is a H atom, carboxyl or alkyl-carbonyl;

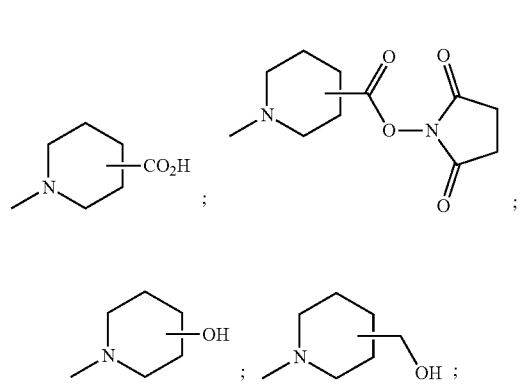

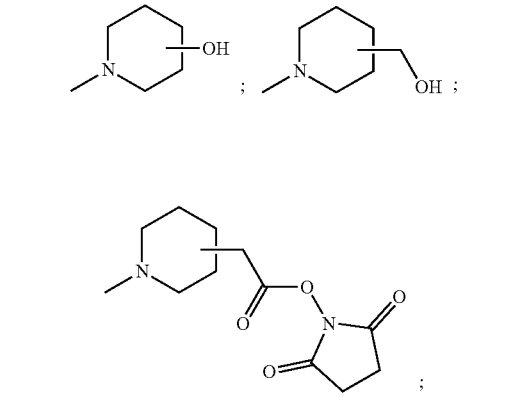

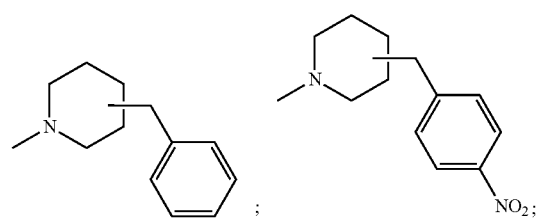

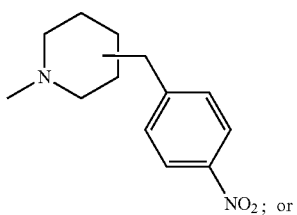

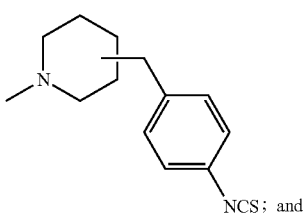

where Z group is selected from:

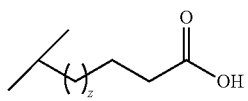

where z=0-18,

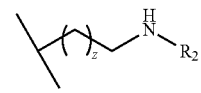

where z=0-18 and R$_2$ is H atom, alkyl, or —(CH$_2$)$_n$—COOH where n=1-10,

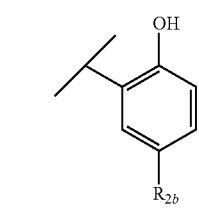

where R$_{2b}$ is H atom, —CH$_3$, —OCH$_3$, —CF$_3$, —COOH, —COON(CO)$_2$(CH$_2$)$_2$, —NO$_2$, —NH$_2$, or —NCS— group,

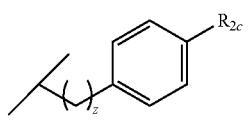

where z=0-18 and R$_{2c}$ is H atom, —NO$_2$, —NH$_2$, or —NCS— group,

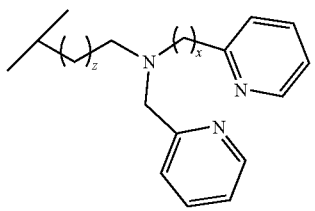

where z=0-18, and x=1-5, where z=1-5, and x=1-5, $R_{2d}$ is H atom, —$CH_3$, —$OCH_3$, —$CF_3$, —$NO_2$, —$NH_2$, —NCS—COOH, or —COON$(CO)_2$ $(CH_2)_2$ group.

12. A complex comprising the compound of claim 11 and a metal selected from Mn(II), Fe(II), Fe(III), Co(II), or Ni(II).

13. A method of imaging, comprising:
applying a compound according to claim 11 as a contrast agent in diagnostic imaging, and performing diagnostic imaging.

14. A contrast agent kit comprising: a compound according to claim 11.

15. A method of imaging, comprising:
applying a complex according to claim 12 as a contrast agent in diagnostic imaging, and performing diagnostic imaging.

16. A contrast agent kit comprising: a complex according to claim 12.

* * * * *